US 12,186,505 B2

(12) United States Patent
Stefanidis

(10) Patent No.: US 12,186,505 B2
(45) Date of Patent: * Jan. 7, 2025

(54) ENDOVASCULAR REMOTELY STEERABLE GUIDEWIRE CATHETER

(71) Applicant: Shuttle Catheters PC, Athens (GR)

(72) Inventor: Giannis Stefanidis, Nea Erythrea Attikis (GR)

(73) Assignee: Shuttle Catheters PC, Athens (GR)

( * ) Notice: Subject to any disclaimer, the term of this patent is extended or adjusted under 35 U.S.C. 154(b) by 0 days.

This patent is subject to a terminal disclaimer.

(21) Appl. No.: 18/229,963

(22) Filed: Aug. 3, 2023

(65) Prior Publication Data

US 2023/0398333 A1    Dec. 14, 2023

Related U.S. Application Data

(63) Continuation of application No. 16/325,652, filed as application No. PCT/GR2017/000025 on May 23, 2017, now Pat. No. 11,738,180.

(30) Foreign Application Priority Data

Aug. 23, 2016   (GR) .............................. 20160100444

(51) Int. Cl.
  *A61M 25/09*   (2006.01)
  *A61B 1/00*    (2006.01)
  (Continued)

(52) U.S. Cl.
  CPC ... *A61M 25/09041* (2013.01); *A61B 1/00098* (2013.01); *A61M 25/0082* (2013.01);
  (Continued)

(58) Field of Classification Search
  CPC ............ A61M 25/09041; A61M 25/01; A61M 25/0133; A61M 25/0136; A61M 25/0138;
  (Continued)

(56) References Cited

U.S. PATENT DOCUMENTS 2,936,760 A    5/1960   Gants
4,627,837 A   12/1986   Gonzalo
(Continued)

FOREIGN PATENT DOCUMENTS

EP         1857039 A2     11/2007
WO    WO 2004/026387      4/2004
(Continued)

OTHER PUBLICATIONS

Intention to Grant for European Application No. 17734447.0, mailed Oct. 24, 2023.
(Continued)

*Primary Examiner* — Kevin C Sirmons
*Assistant Examiner* — Alexandra Lalonde
(74) *Attorney, Agent, or Firm* — Jason H. Vick; Womble Bond Dickinson (US) LLP

(57) ABSTRACT

An endovascular catheter, with a catheter shaft including a first lumen and a shaft opening, a deflection element, and a controlling element. The first lumen and the shaft opening communicate with each other. The deflection element is rotatably arranged inside the catheter shaft, and configured to deflect a guidewire through the shaft opening. The controlling element is operably connected with the deflection element and configured to rotate the deflection element in a first rotating direction. Furthermore, the present invention refers to a catheter assembly with the endovascular catheter and the guidewire.

3 Claims, 8 Drawing Sheets

(51) Int. Cl.
  *A61M 25/00* (2006.01)
  *A61M 25/01* (2006.01)
  *A61M 25/10* (2013.01)
(52) U.S. Cl.
  CPC ...... *A61M 25/0147* (2013.01); *A61M 25/104* (2013.01); *A61M 2025/018* (2013.01)
(58) Field of Classification Search
  CPC .......... A61M 25/0144; A61M 25/0147; A61M 25/0152; A61M 25/0082; A61M 25/0172; A61M 25/104; A61M 25/0067; A61M 25/0074; A61M 25/09; A61M 2025/015; A61M 2025/0161; A61M 2025/0175; A61M 2025/0177; A61M 2025/018; A61M 2025/0079; A61M 2025/0186; A61M 2025/09116; A61B 1/00098
  See application file for complete search history.

(56) References Cited

U.S. PATENT DOCUMENTS

| | | | |
|---|---|---|---|
| 4,998,916 | A | 3/1991 | Hammerslag et al. |
| 5,368,048 | A | 11/1994 | Stoy et al. |
| 5,558,673 | A * | 9/1996 | Edwards ............ A61B 18/1477 606/41 |
| 5,611,777 | A | 3/1997 | Bowden et al. |
| 5,823,961 | A | 10/1998 | Fields et al. |
| 5,830,227 | A | 11/1998 | Fischell et al. |
| 5,919,163 | A | 7/1999 | Glickman |
| 6,743,208 | B1 | 1/2004 | Coyle |
| 6,730,058 | B2 | 5/2004 | Hayzelden |
| 10,702,681 | B2 | 7/2020 | Stefanidis |
| 11,628,283 | B2 | 4/2023 | Stefanidis |
| 11,738,180 | B2 * | 8/2023 | Stefanidis ............ A61M 25/104 604/95.04 |
| 2001/0025174 | A1 | 9/2001 | Daniel et al. |
| 2002/0072706 | A1 | 6/2002 | Hiblar et al. |
| 2004/0215140 | A1 | 10/2004 | Forman |
| 2005/0049455 | A1 * | 3/2005 | Ootawara ................ A61B 1/01 600/107 |
| 2006/0212022 | A1 | 9/2006 | Gellman |
| 2006/0235368 | A1 | 10/2006 | Oz |
| 2007/0005011 | A1 | 1/2007 | Freyman et al. |
| 2007/0142779 | A1 | 6/2007 | Duane et al. |
| 2008/0188800 | A1 | 8/2008 | Bencini et al. |
| 2010/0069834 | A1 | 3/2010 | Schultz |
| 2014/0276135 | A1 | 9/2014 | Agah et al. |
| 2014/0277071 | A1 | 9/2014 | Wu et al. |
| 2016/0067465 | A1 | 3/2016 | Gerrans et al. |
| 2016/0302762 | A1 | 10/2016 | Stigall et al. |
| 2017/0025933 | A1 | 1/2017 | Fujimaki et al. |
| 2017/0079671 | A1 | 3/2017 | Morero et al. |
| 2017/0259033 | A1 | 9/2017 | Erickson |
| 2018/0071088 | A1 | 3/2018 | Badhwar et al. |
| 2019/0209813 | A1 | 7/2019 | Stefanidis |
| 2019/0345959 | A1 | 11/2019 | Tanaka et al. |
| 2019/0388662 | A1 | 12/2019 | Palushi et al. |
| 2023/0218870 | A1 | 7/2023 | Stefanidis |

FOREIGN PATENT DOCUMENTS

| | | |
|---|---|---|
| WO | WO 2005/000388 | 1/2005 |
| WO | WO 2016/170446 | 10/2016 |
| WO | WO 2016/203277 A1 | 12/2016 |

OTHER PUBLICATIONS

U.S. Appl. No. 18/267,031, filed Jun. 13, 2023, Stefanidis.
International Search Report for International Application No. PCT/GR2016/000025, mailed Sep. 13, 2016.
Written Opinion for International Application No. PCT/GR2016/000025, mailed Sep. 13, 2016.
International Preliminary Report on Patentability for International Application No. PCT/GR2016/000025, mailed Dec. 28, 2017.
Intention to Grant for European Application No. 16733176.8, mailed Dec. 18, 2018.
Greek Search Report (Including Translation) for Greek Application No. GR 20150100278, mailed Apr. 13, 2016.
International Search Report for International Application No. PCT/GR2017/000025, mailed Sep. 4, 2017.
Written Opinion for International Application No. PCT/GR2017/000025, mailed Sep. 4, 2017.
International Preliminary Report on Patentability for International Application No. PCT/GR2017/000025, mailed Mar. 7, 2019.
Search Report for corresponding Greek Application No. GR20200100742, mailed Jun. 9, 2021.
International Search Report for International Application No. PCT/GR2021/000031, mailed Nov. 9, 2021.
Written Opinion for International Application No. PCT/GR2021/000031, mailed Nov. 9, 2021.
International Preliminary Report on Patentability for International Application No. PCT/GR2021/000031, mailed Jun. 29, 2023.
International Search Report for International Application No. PCT/GR2021/000032, mailed Nov. 10, 2021.
Written Opinion for International Application No. PCT/GR2021/000032, mailed Nov. 10, 2021.
International Preliminary Report on Patentabiltiy for International Application No. PCT/GR2021/000032, mailed Jun. 29, 2023.
International Search Report for International Application No. PCT/GR2021/000033, mailed Nov. 10, 2021.
Written Opinion for International Application No. PCT/GR2021/000033, mailed Nov. 10, 2021.
International Preliminary Report on Patentability for International Application No. PCT/GR2021/000033, mailed Jun. 29, 2023.
Office Action for U.S. Appl. No. 15/736,009, mailed Nov. 5, 2019.
Notice of Allowance for U.S. Appl. No. 15/736,009, mailed Mar. 4, 2020.
Office Action for U.S. Appl. No. 16/892,025, mailed Aug. 29, 2022.
Notice of Allowance for U.S. Appl. No. 16/892,025, mailed Dec. 8, 2022.
Office Action for U.S. Appl. No. 16/325,652, mailed Oct. 6, 2021.
Office Action for U.S. Appl. No. 16/325,652, mailed Apr. 27, 2022.
Office Action for U.S. Appl. No. 16/325,652, mailed Sep. 8, 2022.
Notice of Allowance for U.S. Appl. No. 16/325,652, mailed Apr. 10, 2023.

* cited by examiner

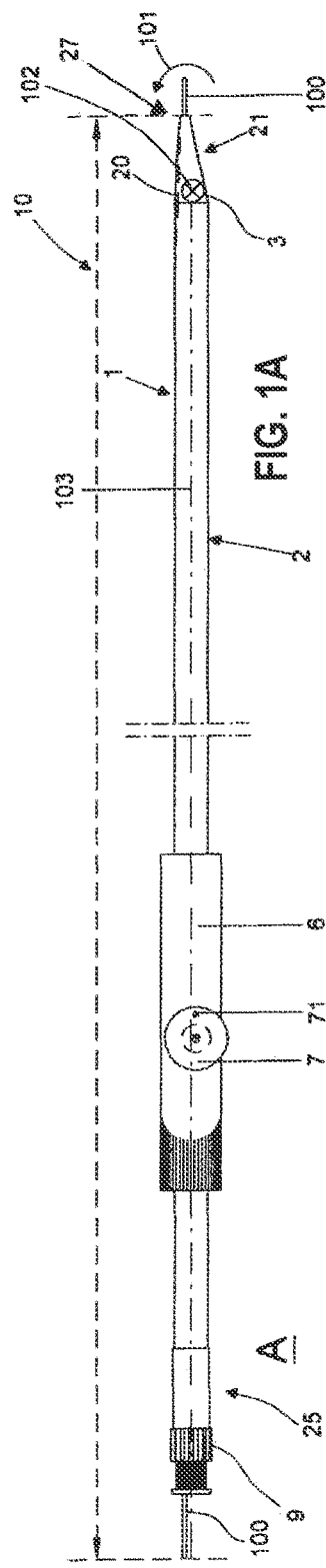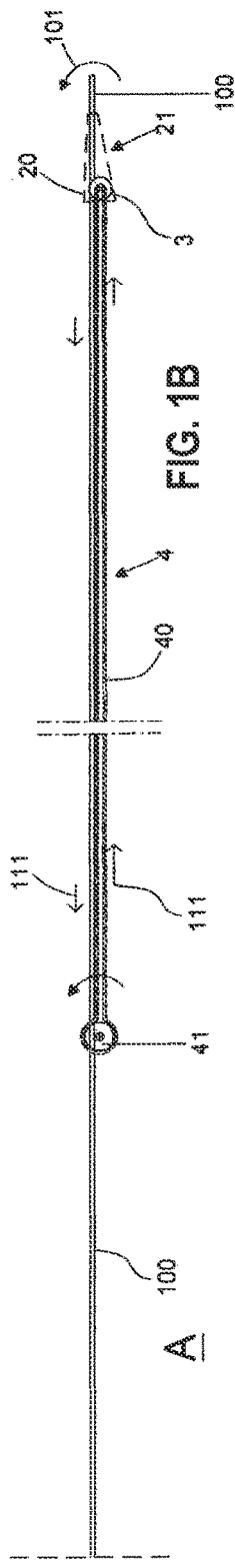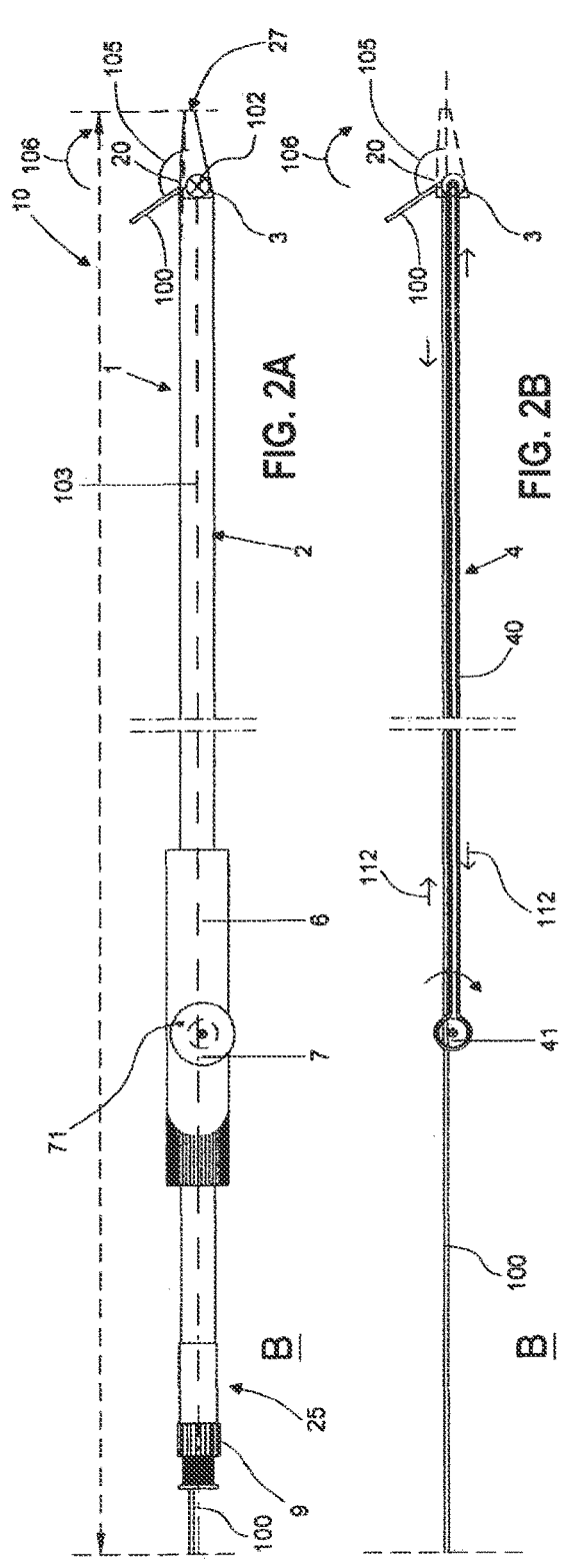

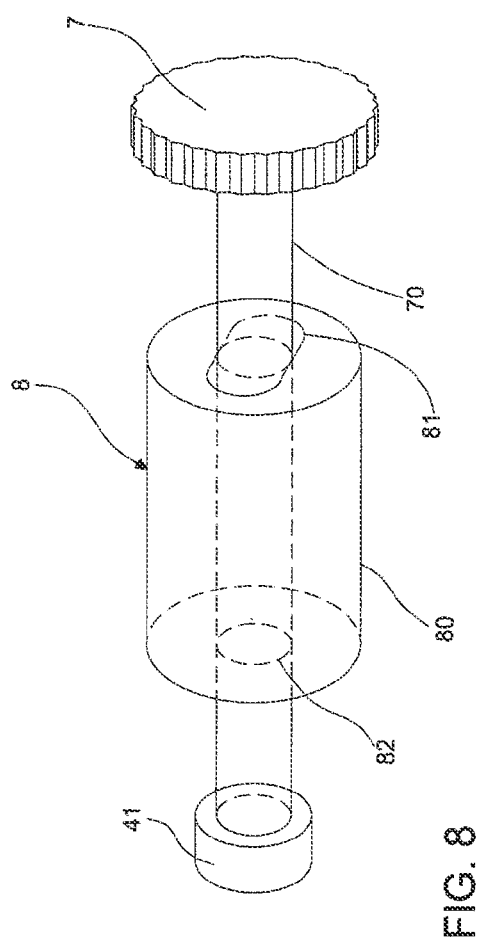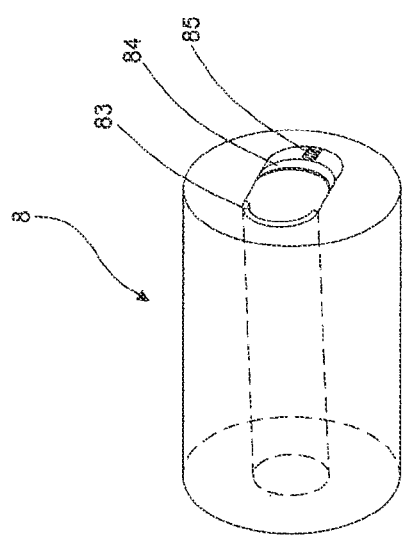
FIG. 8
FIG. 9

ENDOVASCULAR REMOTELY STEERABLE GUIDEWIRE CATHETER

CROSS-REFERENCE TO RELATED APPLICATIONS

This application is a continuation of U.S. patent application Ser. No. 16/325,652, filed Feb. 14, 2019, now U.S. Pat. No. 11,738,180, which is a National Phase Application of International Application PCT/GR2017/000025 filed May 23, 2017, which designated the U.S., which claims priority to Greek patent application Ser. No. 20/160,100444 filed Aug. 23, 2016, each of which are incorporated herein by reference in their entirety.

The present invention refers to minimally invasive surgical devices and minimally invasive surgical methods.

More specifically, the present invention refers to catheters, in particular endovascular catheters, the purpose of which is the steering of a guidewire. Advantageously, the present invention relates to endovascular steerable guidewire catheters that are used in endovascular surgery for the precise positioning of a guidewire within a target vessel or the crossing of the guidewire through a significant tortuosity, a demanding vascular bifurcation, or generally in cases in which the best possible steering of the guidewire is needed. Furthermore, the present invention is concerned with vascular intervention methods during endovascular surgery.

Endovascular surgery is a useful and effective method of dealing with most types of vascular diseases. Generally, an appropriate endovascular device is inserted into the patient's circulatory system, and being guided through the vessels, reaches the site of a target lesion. With the use of endovascular surgery most parts of the patient's circulatory system can be reached, including the heart's coronary vessels, the brain vessels and the peripheral vessels.

Endovascular surgery has the advantage of being a minimally invasive surgical method that was designed to reach, diagnose and treat vessels from within. Due to the minimal invasive character of the endovascular surgery the recanalization of stenoses or blocked vessels can be achieved without the need of general anesthesia, long hospitalization, and considerable postoperative pain.

For the treatment of chronic blockages, stenoses and other vessel pathologies an endovascular surgery method known as angioplasty is often used, which may comprise the deployment of a stent. More particularly during the angioplasty of the coronary, brain or peripheral vessels, an endovascular catheter placed over a guidewire is led to the desired area via the patient's circulatory system. Next, the guidewire, supported by the catheter, is guided through a distal opening of the catheter into the target artery (e.g. coronary, brain, renal artery etc.) until it crosses the stenosis or blockage in need of treatment. Following that, a balloon catheter is moved forward over the guidewire that has already crossed the stenosis and is carefully positioned within the blockage. After the catheter has been carefully positioned, the balloon is inflated to a predefined width, pushing the atheromatic material that causes the blockage outwards and thereby opening the artery. The balloon is then deflated, the blood begins to circulate via the opened artery, and the balloon catheter is removed. When needed, after the artery has been opened, a stent may be deployed at the point of the stenosis in order to keep the vessel open for a longer period of time.

Endovascular catheters with or without the ability to remotely steer the guidewire have been used for years in most endovascular applications and are a basic tool in the aforementioned treatment approaches. Today, many such different catheters are known, of which each one has its specific advantages but also disadvantages.

One of the most important uses of the endovascular steerable guidewire catheters is the backup support and the steering of the guidewire in the doctor's effort to cross through the stenosis or vessel blockage with the catheter. This step proves quite difficult in patients with significant vessel tortuosity, bifurcation and/or vasculature disorders and in general in cases where the guidewire needs the catheter to provide the maximum possible steering support.

Existing catheters are limited in their use in that they cannot be utilized in low-profile blood vessels, i.e. blood vessels with a small cross-section. The reason is that low-profile blood vessels do not allow for a maneuver of the catheter within the vessel. This results in a decreased steering ability of the guidewire, as this depends on the maneuverability of the catheter.

Most existing guidewire catheters have a pre-shaped distal tip in order to facilitate particular catheterization angles. That means that the doctor must choose in advance the catheter—or the combination of catheters—that will be used during the procedure. On one hand this requires a careful planning before the surgery as far as the selection of the appropriate catheter(s) is concerned which, however, incurs high costs and is time consuming. On the other hand this limits the doctor's flexibility, if it turns out during the procedure that another catheter would be more appropriate which however is not available at the time of the surgery or not available at all. In such a case, the doctor will have to abandon the endovascular surgery and revert to an open vascular surgery which poses a higher risk of complications and is associated with a longer rehabilitation period.

Similar considerations apply also to catheters used for other body lumens, through which a catheter needs to be guided. Such a catheter can be used during an endoscopic retrograde cholangiopancreatography and more widely during the endoscopic treatment of cholangi. Additionally, it can be used during endoscopic urinary tract procedures, such as cystoscopy or/and diagnostic and treatment procedures of ureteral obstruction, filling defects and anomalies via retrograde radiography, ureterostomy, etc. Furthermore, it can be used during endoscopic sinus surgery, microlaryngial surgery and eardrum repair surgery. Moreover, it can be used for transbronchial procedures such as biopsies, airway stent placement and balloon dilatation procedures.

For the reasons described above, there is a great need to develop an alternative catheter that overcomes the disadvantages of existing catheters while maintaining any of their advantages.

It is in particular an object underlying the present invention to suggest a catheter, more specifically an endovascular catheter, with an increased ability of steering a guidewire while maintaining its pushability and trackability over the guidewire in tortuous body lumens, more specifically in tortuous vasculature.

In the field of catheters the term "steering ability" (steerability) generally refers to the shaft of the catheter and more specifically means the ability of the catheter shaft to be steered. This essentially means a high resistance to bending/folding of the catheter shaft during its rotation within a lumen, e.g. vessel (high torque control). In other words, the term "steerability" refers to the ability to turn or rotate the distal end of the catheter shaft with like-for-like movement of the proximal section of the catheter shaft or a catheter handle. It is achieved through strong torque transfer along the length of the catheter shaft. In the framework of the present invention this term is used with reference to the guidewire and with the more general meaning of the guidewire being able to be guided inside a lumen. This in turn leads to an increased guidance of the catheter shaft inside a lumen since the catheter shaft moves over the guidewire.

By the term "pushability" the degree in which the force transmitted from a proximal end of the catheter is translated into movement of a catheter's distal end (catheter tip), which depends on the transmission of the force along the body of the catheter, is understood. In other words the term "pushability" means the ease of advancing the catheter inside a lumen, e.g. vessel, and is indicative of the amount of force the distal tip of the catheter sees when a known force is being applied to the catheter on its proximal end.

The term "trackability" means the ability of a catheter to follow the guidewire in tortuous lumens, e.g. vessels, which depends on the diameter, length and elasticity of the catheter, as well as the resistance caused by friction between the catheter and the lumen. In other words, the term "trackability" means the ability of the catheter to track over a guidewire during insertion around bends in the vessel and can be quantified by measuring the force needed to advance the catheter through a tortuous lumen.

A further object underlying the present invention lies in providing an easy-to-build and easy-to-use catheter with increased steering potential without lacking pushability and trackability over a guidewire in tortuous lumens, more specifically in tortuous vasculature.

These objects are achieved by features as disclosed herein.

Advantageously, these objects are achieved by a catheter that incorporates a deflection element that has the ability to rotate around an axis. The deflection element is configured to deflect a guidewire.

More specifically, the inventive catheter, more particularly an endovascular catheter, comprises a catheter shaft having a first lumen and a shaft opening, a deflection element, and a controlling element. The first lumen and the shaft opening communicate with each other. The deflection element is rotatably arranged inside the catheter shaft, and configured to deflect a guidewire through the shaft opening. The controlling element is operably connected with the deflection element and configured to rotate the deflection element in a first rotating direction.

The deflection element incorporated in the catheter shaft changes an exit angle of the guidewire in a controlled way. In this manner the guidewire can exit the catheter shaft forming at will a wide range of angles in relation to a longitudinal axis of the catheter shaft. This practically means that the guidewire can be accurately steered through big angulations with a high performance even within very low-profile body lumens, because the catheter shaft does not have to be angled to steer the guidewire. Furthermore, the proposed catheter is advantageous as it can replace the catheters that have a pre-shaped exit angle for the guidewire and thus, a procedure can be performed with the use of one and only catheter. By providing such a deflection element the catheter exhibits an increased steering (rotation) ability of its guidewire without losing its pushability and trackability, as the deflection element is arranged inside the catheter shaft, and thus, does not affect the properties of the catheter shaft. Therefore, already proven properties for a catheter shaft with regard to pushability and trackability can be maintained. Due to the deflection of the guidewire instead of the catheter shaft as well as the internal arrangement of the deflection element in the catheter shaft for deflecting the guidewire, the diameter of the catheter shaft can be significantly reduced. Hence, the inventive catheter can be used in a wide range of applications e.g. in the cardiovascular or urological fields. Such an application is to use the catheter for directing a medical device to a particular part of the body for minimally invasive diagnoses and treatment procedures. For example, the catheter of the present invention can be loaded with other endovascular tools such as embolization coils, and facilitate their placement within the vessel, or even contribute with its steering to the reentry of the guidewire from the sub-intimal layer of a vessel into the true lumen of the vessel during a sub-intimal technique procedure. Moreover, reducing the diameter of the catheter shaft enables minimising the size the patient's entry wound resulting thereby in fewer complications and a lower risk of infection. The catheter according to the present invention can support and steer the guidewire in the effort to move through anatomically-hard-to-cross regions of vessels or other lumens of the human body, while at the same time accurately readjusting the exit angle of the guidewire.

The dependent claims contain advantageous embodiments of the present invention.

Preferably, the deflection element is configured to rotate around a rotational axis which is vertical to a longitudinal axis of the catheter shaft. More preferably, the deflection element is configured to rotate around a rotational axis which is arranged horizontally when the longitudinal axis of the catheter shaft is arranged horizontally. In other words, the rotational axis of the deflection element preferably lies in a horizontal plane when the longitudinal axis of the catheter shaft also lies in a horizontal plane.

Advantageously, the controlling element is configured to rotate the deflection element in a second rotating direction opposite to the first rotating direction.

In a preferred embodiment, the controlling element can be rigid, wherein the controlling element is configured to rotate the deflection element in both the first rotating direction and the second rotating direction. For instance, the controlling element is formed as a rigid rod or bar.

In a better preferred embodiment, the controlling element is formed as a closed-loop transmission element, which is configured to transmit a rotation from a rotating element to the deflection element, wherein the rotating element is operably connected to the transmission element. In other words, the deflection element is connected to the rotating element by the closed-loop transmission element, so that a rotation from the rotating element is transmitted to the deflection element. Expressed differently, the controlling element is in the form of a closed circuit (closed inner circuit). With the proposed arrangement both a rotation in the first rotating direction and the second rotating direction can be effected with a single element which makes use of the catheter easier. Thus, the user of the catheter has to just operate the closed-loop transmission element for deflecting the guidewire in both the first and second rotating directions.

The closed-loop transmission element is preferably arranged in such a way that the rotating element and the deflection element are rotated in the same direction. This facilitates an intuitive use of the catheter from a user e.g. a surgeon, as for example a rotation of the rotating element in the counterclockwise direction causes a rotation of the deflection element also in the counterclockwise direction. Therefore, the user of the catheter can easily perceive the effect of his action when the rotating element is rotated, e.g. through a rotating button or knob connected to the rotating element.

In another embodiment, the controlling element comprises a first controlling element and a second controlling element, wherein the first controlling element and the second controlling element are operably connected with the deflection element and configured to rotate the deflection element in the first rotating direction and the second rotating direction, respectively, wherein the second rotating direction is opposite to the first rotating direction. By providing such a second controlling element, the rotation of the deflection element in the second rotating direction can be unlinked or separated from the rotation of the deflection element in the first rotating direction.

In an embodiment of the present invention, the second controlling element is configured to rotate the deflection element also in the first rotating direction. As described with respect to the first controlling element, the second controlling element can be rigid so that the second controlling element can rotate the deflection element in both the first rotating direction and the second rotating direction. For instance, the second controlling element is formed as a rigid rod or bar.

If both the first controlling element and the second controlling element are configured to rotate the deflection element in both the first rotating direction and the second rotating direction, both controlling elements can share the force applied by a user in order to rotate the deflection element in any of the rotating directions.

Preferably, the rotating element and the deflection element are formed in such a way, that a rotation of the rotating element is transmitted to the deflection element with a transmission ratio equal to or higher than 1. The transmission ratio is defined as the ratio of the rotational speed of the deflection element to the rotational speed of the rotating element.

More particularly, the rotating element is formed as a first rotating disc.

Preferably, the rotating element is connected with a rotating button or knob, so that rotating of the rotating button or knob causes rotation of the rotating element. In particular, a diameter of the rotating button or knob is larger than the diameter of the rotating element.

Furthermore, the deflection element preferably comprises a second rotating disc, which is operably connected with the first rotating disc by the closed-loop transmission element.

In particular, a diameter of the first rotating disc is equal to or greater than a diameter of the second rotating disc. The transmission ratio can be defined as the ratio of the diameter of the first rotating disc to the diameter of the second rotating disc.

More specifically, the closed-loop transmission element is a thread, more particularly synthetic thread. Using a thread, in particular synthetic thread is advantageous as the closed-loop transmission element of the catheter can thereby have a high-tensile strength and is lightweight. Alternatively, other mechanical elements such a wire, a belt and the like could be used as the close-loop transmission element.

Alternatively, the rotating element can be formed as a first pulley. Also, the deflection element may comprise a second pulley, which is operably connected with the first pulley by the closed-loop transmission element. In particular, a diameter of the first pulley is equal to or larger than a diameter of the second pulley. The closed-loop transmission element can be formed as a belt.

Advantageously, the deflection element may comprise a recess formed in the direction of the longitudinal axis of the catheter shaft, wherein more particularly a guiding element configured to guide the guidewire is arranged at a distal end of the recess. The recess serves to receive the guidewire. The guiding element guides the guidewire and contributes thereby to its more accurate navigation inside a body lumen.

The recess is preferably formed centrally in a widthwise direction of the deflection element, wherein the widthwise direction is parallel to the rotational axis of the deflection element.

According to an embodiment, the guiding element is formed as an integral part of the deflection element. In this case, the recess preferably extends from a proximal end of the deflection element to the guiding element.

Alternatively, the guiding element can be a separate element attached to the deflection element at a distal end of the deflection element. In this case, the recess preferably extends over the whole length from the proximal end to the distal end of the deflection element.

More specifically, the guiding element is formed as a ring, arranged in such a way that a central axis of the ring coincides with a longitudinal axis of the recess.

The guiding element is preferably configured to apply a first force to the guidewire, when the deflection element is rotated in the first rotating direction. Also, the guiding element is preferably configured to apply a second force to the guidewire, when the deflection element is rotated in the second rotating direction. A component of the first force in the direction of an axis which is vertical to the longitudinal axis of the catheter shaft and the rotational axis of the deflection element is opposite to a component of the second force in the direction of said axis.

The deflection element is preferably formed as a sphere or a cylinder. In the case of the deflection element being formed as a cylinder, the cylinder axis extends in the direction of the rotational axis of the deflection element.

Preferably, the recess comprises a bottom face, which is curved, more particularly concave when viewed from a longitudinal axis of the recess. Therefore, the guidewire can be received in the recess without having to sharply bend or kink, especially when the deflection element is rotated in order to deflect the guidewire.

The recess is preferably formed in such a way, that the guidewire touches only partially the bottom face of the surface, when the guidewire extends in the longitudinal axis of the catheter shaft, that is, when the guidewire is not deflected. More specifically, the recess is preferably formed in such a way that a bottom part of the guidewire facing the bottom face of the recess touches only a proximal edge and a distal edge of the recess, when the guidewire is not deflected, i.e. presents zero deflection.

The bottom face comprises in particular a first plane of curvature which is defined by a longitudinal axis of the recess and an axis vertical to the longitudinal axis of the recess and the rotational axis of the deflection element.

More preferably, the bottom face of the recess further comprises a second plane of curvature, which is vertical to the first plane and defined by the longitudinal access of the recess and the rotational axis of the deflection element.

The longitudinal axis of the recess is preferably parallel to the longitudinal axis of the catheter shaft.

Advantageously, the bottom face of the recess is concave in both planes of curvature when viewed from the longitudinal axis of the recess and/or the rotational axis of the deflection element.

The curvature of the recess in the first plane of curvature enables the guidewire to be smoothly received in the recess. The curvature in the first plane of curvature is advantageous, as it enables the guidewire to be smoothly received in the recess, when the guidewire is deflected by rotating the deflection element. This means that, when the guidewire is deflected by rotating the deflection element, the guidewire substantially touches the whole bottom face of the deflection element. Preferably, the curvature in the second plane of curvature is smaller than the curvature of the guidewire, that is, a radius of curvature in the first plane of curvature is larger than a radius of the guidewire.

Preferably, a maximum angle of rotation of the deflection element is 170o from a start position. In particular, the start position corresponds to a position in which the longitudinal axis of the recess is parallel to longitudinal axis of the catheter shaft. In the start position the guidewire is not deflected and lies straight in the recess of the deflection element.

The catheter shaft preferably comprises a tip, wherein the tip is shaped as a frustum of a cone, more particularly a frustum of an oblique cone. This specific shape of the tip facilitates the insertion and the advancement of the catheter into a lumen. The tip can be formed as a separate part attached to or integral with the rest of the catheter shaft.

More specifically, the deflection element is arranged inside the tip of the catheter shaft. By this arrangement, a great range as far as the exit angle of the guidewire is concerned can be achieved. The term "exit angle of the guidewire" can also be understood as "deflection angle of the guidewire".

The shaft opening preferably comprises a first shaft opening, i.e. a single shaft opening, at a distal end of the catheter shaft. The first shaft opening is more particularly arranged at a distal face of the catheter shaft. The distal face of the catheter shaft corresponds to the distal face of the tip of the catheter shaft. Preferably, the first shaft opening is essentially arranged vertically to the longitudinal axis of the catheter shaft.

In addition to the first shaft opening the shaft opening preferably comprises a second shaft opening that extends in the direction of the longitudinal axis of the catheter shaft and is preferably formed on a peripheral area of the catheter shaft. In other words the shaft opening preferably comprises the first and the second shaft openings. More specifically, the second shaft opening is arranged on a peripheral area of the tip of the catheter shaft. The first shaft opening and the second shaft opening preferably communicate with each other.

Thus, the guidewire can be easily deflected through the shaft opening when the deflection element is rotated.

Advantageously, the catheter shaft comprises the first lumen configured to receive the guidewire, and/or a second lumen configured to receive the controlling element.

More specifically, the first lumen and/or the second lumen extend in the direction of the longitudinal axis of the catheter shaft. This makes the construction of the catheter shaft easier. Thus, the first lumen and/or the second lumen can be easily constructed by drilling into the catheter shaft.

The longitudinal axis of the recess preferably coincides with a longitudinal axis of the first lumen, which is configured to receive the guidewire, when the deflection element is not rotated, i.e. when the guidewire is not deflected.

Alternatively, the catheter shaft may be provided with a single lumen (namely, the first lumen), configured to receive both the guidewire and the controlling element. In this case, guiding/support elements can further be provided for guiding/supporting the guidewire.

Most preferably, the recess is formed in such a way that the recess always faces and/or communicates with the first lumen. "Always" can be understood as "over the whole allowable range of rotation of the deflection element or over the whole range of exit angles of the guidewire". In other words, the first lumen is always in alignment and communication with the recess.

The present invention relates also to a catheter assembly, comprising a catheter as described above and a guidewire. The advantages described with reference to the catheter are also given for the catheter assembly.

A further aspect of the present invention concerns a minimally invasive surgical method, in particular a method of reaching a target site inside a body lumen using the aforementioned catheter assembly. More specifically, the present invention relates to a method of inserting and/or steering a guidewire or a catheter assembly as described above inside a body lumen.

It is further noted that the term "proximal" means "further away from the patient's body" when the catheter is used, whereas the term "distal" means "closer to the patient's body" when the catheter is used. For example, a proximal end of the catheter shaft is the end of the catheter shaft which is situated away from the patient's body when the catheter is used on the patient's body. On the other hand, a distal end of the catheter shaft is the end which is nearer the patient's body when the catheter is used on the patient's body.

These and further details, advantages and features of the present invention will be described based on embodiments of the invention and by taking reference to the accompanying figures, in which same or similar reference signs denote same or similar elements or elements having same or similar functions. The figures show:

FIG. 1a a simplified schematic front view of a catheter assembly with a catheter according to a first embodiment of the present invention in a first position;

FIG. 1b a simplified schematic front view of the catheter assembly of FIG. 1a, wherein a catheter shaft has been removed for illustrative purposes;

FIG. 2a a simplified schematic front view of a catheter assembly according to the first embodiment of the present invention in a second position;

FIG. 2b a simplified schematic front view of the catheter assembly of FIG. 2a, wherein a catheter shaft has been removed for illustrative purposes;

FIG. 3 a simplified schematic perspective view of the catheter assembly according to the first embodiment;

FIG. 4 a simplified schematic cross-sectional view of the catheter assembly of the first embodiment;

FIG. 5 a simplified schematic perspective view of a deflect element of the catheter assembly according to the first embodiment, in which a guidewire is arranged;

FIG. 6 a simplified schematic perspective view of the deflect element of FIG. 5 without the guidewire;

FIG. 7 a simplified schematic perspective view of a part of a controlling element of the catheter assembly of the preceding figures;

FIG. 8 a simplified schematic perspective view of a stop mechanism of the catheter;

FIG. 9 a simplified schematic perspective view of a part of the stop mechanism of FIG. 8;

FIG. 10 a simplified schematic perspective view of a tip of the catheter shaft from the front;

FIG. 11 a simplified schematic perspective view of the tip of the catheter shaft of FIG. 10 from below;

FIG. 12 a simplified schematic cross-sectional view of the tip of the catheter shaft of FIGS. 10 and 11;

FIG. 13 a simplified schematic perspective view of a deflect element according to a second embodiment of the present invention;

FIG. 14 a simplified schematic perspective view of a tip of the catheter shaft from the front according to a third embodiment of the present invention; and FIG. 15 a simplified schematic cross-sectional view of the tip of the catheter shaft of FIG. 14.

In the following, embodiments and the technical background of the present invention are presented in detail by taking reference to accompanying FIGS. 1 to 15. Identical or equivalent elements and elements which act identically or equivalently are denoted with the same reference signs. Not in each case of their occurrence a detailed description of the elements and components is repeated.

The depicted and described features and further properties of the invention's embodiments can arbitrarily be isolated and recombined without leaving the gist of the present invention. It is also noted that the figures are not necessarily drawn in scale.

In the following a catheter assembly 10 with a catheter 1 according to a first embodiment of the present invention will be described with reference to FIGS. 1 to 12.

As can be seen from FIGS. 1a, 1b and 2a, 2b, the catheter assembly 10 comprises the catheter 1 and a guidewire 100. The guidewire 100 acts as a guide which the catheter 1 can rapidly follow for easier delivery to a target site in the body of a patient. The target site can be e.g. a vessel with a lesion or in general any body lumen that requires a treatment.

The catheter assembly 10 also has an adapter 9, which is connected to a catheter shaft 2 at a proximal region of the catheter shaft 2, preferably at a proximal end 25 of the catheter shaft 2. The proximal region of the catheter shaft 2 is the region of the catheter shaft 2 which is further away from the patient's body when the catheter 1 is inserted in the patient's body. Accordingly, the proximal end 25 is the end of the catheter shaft 2 which is further away from the patient's body when the catheter 1 is inserted in the patient's body. The adapter 9 is configured to connect other instruments or devices with the catheter 1. For example, a syringe can be connected via the adapter 9 to the catheter shaft 2 in order to remove the air from the first lumen (during the preparation of the catheter, before it is inserted in the patient's body) and/or deliver radiopaque contrast media or medication.

In detail, the catheter 1 comprises the catheter shaft 2 with a shaft opening. The shaft opening comprises a first shaft opening 26 and a second shaft opening 20. The catheter shaft 2, which has a longitudinal axis 103, is preferably of cylindrical shape. Advantageously, the catheter shaft 2 is made of flexible material, so that it can follow the shape of the body lumen, into which the catheter shaft 2 is inserted. Furthermore, the catheter shaft 2 is advantageously partially made of a radiopaque material.

The catheter 1 also comprises a deflection element 3, which is rotatably arranged inside the catheter shaft 2, and configured to deflect the guidewire 100 through the shaft opening.

By deflecting the guidewire 100 through the shaft opening, an exit angle (deflection angle) of the guidewire 100 can be changed so that the catheter 1 can be placed into body lumens with orifices of significant angulations.

In order to deflect the guidewire 100, a controlling element 4 is provided. The controlling element 4 is operably connected with the deflection element 3 and configured to rotate the deflection element 3 in a first rotating direction 101. Preferably, the controlling element 4 is also configured to rotate the deflection element 3 in a second rotating direction 106. The second rotating direction 106 is opposite to the first rotating direction 101.

It is noted that FIGS. 1b and 2b differ from the FIGS. 1a and 2a, respectively, in that in FIGS. 1b and 2b the catheter shaft 2 is removed for illustrative purposes, thereby revealing the controlling element 4.

Also, FIGS. 1a and 1b show the catheter 1 in an un-deflected state (first state) A of the guidewire 100, whereas the guidewire 100 is presented in a deflected state (second state) B in FIGS. 2a and 2b. The arrows referring to the first rotating direction 101 in FIGS. 1a and 1b indicate how the deflection element 3 should be rotated so that the guidewire 100 is brought from the un-deflected state A to the deflected state B in FIGS. 2a and 2b. Accordingly, the arrows referring to the second rotating direction 106 in FIGS. 2a and 2b indicate how the deflection element 3 should be rotated so that the guidewire 100 is brought from the deflected state B to the un-deflected state A in FIGS. 1a and 1 b.

Advantageously, the catheter shaft comprises a first lumen 23 configured to receive part of the guidewire 100, and a second lumen 24 configured to receive part of the controlling element 4 (FIGS. 3 and 4). More specifically, the first lumen 23 and the second lumen 24 extend in the direction of the longitudinal axis 103 of the catheter shaft 2. Especially, the first lumen 23 and/or the second lumen 24 are formed by removing material from the catheter shaft 2, in particular by drilling. Thus, the catheter shaft 2 is preferably formed as a solid element having hollow areas corresponding to the first lumen 23 and the second lumen 24. Most preferably, the fist lumen 23 extends from the proximal end 25 of the catheter shaft 2 till the beginning of the deflection element 3 in the direction of the longitudinal axis 103, when seeing the deflection element 3 from the distal end of the catheter shaft 2. Further, the second lumen 24 is preferably shorter in length in the direction of the longitudinal axis 103 than the first lumen 23.

The catheter shaft 2 preferably comprises a tip 21, wherein the tip 21 is shaped as a frustum of an oblique cone (FIGS. 1, to 4 and 10 to 12). This specific shape of the tip 21 facilitates the insertion and the advancement of the catheter 1 into a body lumen. The tip 21 of the catheter shaft 2 receives the deflection element 3 in its interior. To serve this purpose, the tip 21 is preferably hollow. Further, the tip 21 can be attached to or be made integral with the rest of the catheter shaft 2. The tip 21 corresponds to the distal region of the catheter shaft 2.

As already described, the shaft opening comprises a first shaft opening 26 and a second shaft opening 20. The first shaft opening 26 and the second shaft opening 20 are formed at the tip 21 of the catheter shaft 2.

More specifically, the first shaft opening 26 is arranged at a distal end 27 of the catheter shaft 2. The first shaft opening 26 is arranged essentially vertically to the longitudinal axis 103 of the catheter shaft 2. The distal end 27 of the catheter shaft 2 corresponds to the distal face of the tip 21 of the catheter shaft 2.

Further, the second shaft opening 20 extends in the direction of the longitudinal axis 103 of the catheter shaft 2 and is formed on a peripheral area 22 of the catheter shaft 2. More specifically, the second shaft opening 20 is arranged at the side/region of the tip 21 where the frustum of the oblique cone has a smaller inclination.

Thus, the guidewire 100 can be easily deflected through the shaft opening 20 when the deflection element 3 is rotated.

As can mainly be seen from FIGS. 10 to 12, the first shaft opening 26 communicates with the second shaft opening 20.

A maximum angle 105 of rotation of the deflection element 3 between the un-deflected state A and the deflected state B of the guidewire 100 is preferably 170°. In the un-deflected state A, the guidewire 100 has an exit angle of Go. In other words, in the un-deflected state A the guidewire 100 extends in the direction of the longitudinal axis 103 of the catheter shaft 2. The un-deflected state A corresponds to a start position of the deflection element 3. In the start position the deflection element 3 has a rotation angle of Go. An end position of the deflection element 3 corresponds to the deflected state B of the guidewire 100. Thus, a maximum exit angle of the guidewire 100 through the shaft opening is preferably 170°.

The deflection element 3 and the guidewire 100 can have a rotation angle and an exit angle, respectively, between 0o and 170o.

Therefore, the guidewire 100 can be navigated into a wide range of lumens with orifices of significant angulations and thus the catheter 1 can be used for many different applications.

The deflection element 3 is preferably configured to rotate around a rotational axis 102 which is vertical to a longitudinal axis 103 to of the catheter shaft 2 (FIGS. 1 and 3). When the longitudinal axis 103 of the catheter shaft 2 lies in a horizontal plane, the deflection element 3 is preferably arranged in such a way that the rotational axis 102 also lies in a horizontal plane.

Further, the deflection element 3 is preferably rotatably arranged inside the tip 21 of the catheter shaft 2. For this reason, the deflection element 3 preferably comprises supports 92, which are each in the form of a shaft. The tip 21 is provided with plain bearings, which are preferably formed as openings in the tip 21.

As best seen from FIGS. 1 and 3, the controlling element 4 is preferably formed as a closed-loop transmission element 40. The closed-loop transmission element 40 is configured to transmit a rotation from a rotating element 41 to the deflection element 3, wherein the rotating element 41 is operably connected to the closed-loop transmission element 40. The closed-loop transmission element 40 is basically a linear transmission element, which means that the closed-loop element 40 basically makes a linear motion. This is denoted by arrows 111 and 112 in FIGS. 1(b) and 2(b), respectively.

The rotating element 41 is more particularly formed as a first rotating disc.

Preferably, the rotating element 41 is connected with a rotating button 7 (rotating remotely steering button) via an axis 70 (FIGS. 3 and 7), so that rotating the rotating button 7 causes a rotation of the rotating element 41, more specifically in the same direction. This means that a rotation of the rotating button 7 in the first rotating direction 101 (in the second rotating direction 106) causes a rotation of the first rotating element 41 in the first rotating direction 101 (in the second rotating direction 106).

As can be seen from FIG. 4, the catheter shaft 2 comprises a third lumen 28 which extends to the periphery of the catheter shaft 2 and through which the axis 70 passes. The third lumen 28 may also communicate with the second lumen 24

Furthermore, a diameter of the rotating button 7 is larger than the diameter of the rotating element 41. Due to the bigger size of the rotating button 7 it is easier for the user to adjust the exit angle of the guidewire 100, while the catheter shaft 2 can be made more compact due to the smaller size of the rotating element 41.

Moreover, the deflection element 3 preferably comprises a second rotating disc 42, which is operably connected with the first rotating disc (rotating element 41) by the closed-loop transmission element 40.

In particular, a diameter of the first rotating disc is equal to or greater than a diameter of the second rotating disc 42. The transmission ratio between the first rotating disc and the second rotating disc 42, which can be defined as the ratio of the diameter of the first rotating disc to the diameter of the second rotating disc 42, is preferably equal or greater than 1.

Alternatively, the deflection element 3 may comprise a ring-shaped nut, at the position of which the closed-loop transmission element 40 is wound up around the deflection element 3.

The rotating button 7 further comprises an orientation indicator 71 that indicates the orientation of the deflection element 3 and thus the orientation of the guidewire 100. The orientation indicator 71 can be e.g. an arrow-like element attached to the rotating button 7 or an arrow-like marker painted or formed on the rotating button 7. Therefore, the user of the catheter assembly 1 can at any time identify whether the guidewire 100 is deflected and get at least a general idea of the extent to which the guidewire 100 is deflected. A scale showing values for the exit angle of the guidewire 100 can also be provided. The orientation indicator 71 together with the scale could then be understood as a position indicator.

Preferably, the catheter 2 further comprises a handle 6 which is arranged around the catheter shaft 2. In particular, the handle 6 envelopes a region of the catheter shaft 2. The handle 6 provides the user with an increased holding control of the catheter 1 for a safe, efficient, and consistent procedure. Further, the handle 6 comprises a channel which communicates with the third lumen 28 and through which the axis 70 passes to connect to the rotating button 7. Thus, the rotating button 7 is arranged at the handle 6.

The transmission element 40 is preferably arranged in such a way that the rotating element 41 and the deflection element 3 are rotated together in the same direction. This means that, for example, when the rotating element 41 is rotated in the first rotating direction 101 by rotating the rotating button 7 in the first rotating direction 101, the deflection element 3 is also rotated in the first rotating direction 101. Accordingly, a rotation of the rotating element 41 in the second rotating direction 106 causes a rotation of the deflection element 3 also in the second rotating direction 106.

A different configuration is also possible. For instance, the transmission element 40 can be arranged in such a way that the rotating element 41 and the deflection element 3 are rotated in opposite directions. This would for example be the case, when the transmission element 40 is arranged in a cross-wise manner so that a rotation of the rotating element 41 in the first rotating direction 101 causes a rotation in the second rotating direction 106.

More specifically, the closed-loop transmission element 40 is a synthetic thread. Using a synthetic thread is advantageous as it is a high-tensile strength and lightweight material. Therefore, a fail-safe operation of the deflection element 3 can be ensured without an increase in the overall weight of the catheter 1.

Advantageously, the deflection element 3 comprises a main body 35, in which a recess 30 is formed in the direction of the longitudinal axis 103 of the catheter shaft 2. The main body 35 of the deflection element 3 is of spherical shape in the present embodiment. To be more concrete, the outer shape of the main body 35 is a sphere.

FIGS. 5 and 6 show that the recess 30 is preferably formed centrally in a widthwise direction of the deflection element 3, wherein the widthwise direction corresponds to the rotational axis 102 of the deflection element 3.

Preferably, the recess 30 comprises a bottom face 33, which is curved, more particularly concave when viewed from a longitudinal axis 104 of the recess 30. The longitudinal axis 104 of the recess 30 is preferably parallel to the longitudinal axis 103 of the catheter shaft 2 when the deflection element 3 is in its start position, where the guidewire 100 is not deflected.

The bottom face 33 connects a first wall 38 of the recess 30 and a second wall 39 of the recess 30. The first wall 38 and the second wall 39 are preferably parallel to each other and extend vertically to the longitudinal axis 103 of the catheter shaft 2 and the rotational axis 102 of the deflection element 3.

The bottom face 33 comprises in particular a first plane 107 of curvature which is defined by the longitudinal axis 104 of the recess 30 and an axis vertical to the longitudinal axis 104 of the recess 30 and the rotational axis 102 of the deflection element 3 (FIG. 6). An intersection 108 of the bottom face 33 and the first plane 107 is a concave curve when viewed from the longitudinal axis 104 of the recess 30.

Also, the bottom face 33 of the recess 30 further comprises a second plane 109 of curvature, which is vertical to the first plane of curvature 107 and defined by the longitudinal access 104 of the recess 30 and the rotational axis 102 of the deflection element 3. An intersection 110 of the bottom face 33 and the second plane 109 is a concave curve when viewed from the rotational axis 102 of the deflection element 3. More specifically, the curvature in the second plane 109 of curvature is chosen to be at least equal to the curvature of the guidewire 100.

The recess 30 is preferably formed in such a way, that the guidewire 100 partially touches the bottom face 33 of the recess 30, when the guidewire 100 extends in the longitudinal axis 103 of the catheter shaft 2. In this position, the guidewire 100 is not deflected. In other words, the recess 30 is preferably formed in such a way that a bottom part of the guidewire 100 facing the bottom face 33 of the recess 30 touches only a proximal edge 36 and a distal edge 37 of the recess 30 (FIG. 6), when the guidewire 100 presents zero deflection. In that sense, the proximal edge 36 and the distal edge 37 of the recess 30 are considered part of the bottom face 33.

Most preferably, the recess 30 is formed in such a way that the recess 30 always faces and/or communicates with the first lumen 23 between the start position and the end position of the deflection element 3.

Preferably, a guiding element 31 configured to guide the guidewire 100 is arranged at a distal end 91 of the recess 30 (FIG. 6). More particularly, the guiding element 31 is formed as an integral part of the deflection element 3. In this case, the recess 30 preferably extends in the direction of the longitudinal axis 104 from a proximal end 90 of the deflection element 3 to the guiding element 31. The proximal end 90 of the deflection element 3 corresponds to a proximal end of the recess 30.

More specifically, the guiding element 31 is formed as a ring, arranged in such a way that a central axis of the ring coincides with the longitudinal axis 104 of the recess 30. The guidewire 100 goes through the guiding element 31 in order to be guided.

Alternatively, the guiding element 31 can be a separate element attached to the deflection element 3 at a distal end of the deflection element 3. In this case, the recess 30 preferably extends in the direction of the longitudinal axis 104 over the whole length of the deflection element 3 from the proximal end 90 to the distal end of the deflection element 3.

As shown in FIG. 7, in order to secure the position of the guidewire 100, the catheter shaft 2 is provided with a stop mechanism 8. The stop mechanism allows for increased maneuvering or handling abilities for the user of the catheter 1, as the user does not need to constantly hold the rotating button 7 for securing a chosen position of the guidewire 100. The stop mechanism 8 is explained in more details with reference to FIGS. 8 and 9. For the sake of a better overview, the stop mechanism 8 has been omitted from FIGS. 3 and 4.

According to FIG. 8, the stop mechanism 8 preferably comprises a body 80 with a first opening 81 and a second opening 82 for the axis 70 to go through. The body 80 is preferably cylindrical and hollow. The body 80 is preferably attached to the catheter shaft 2, what is not drawn for illustrative purposes.

The first opening 81 is bigger in terms of its cross-section than the second opening 82. More particularly, the second opening 82 is circular and has a diameter (slightly) bigger than the diameter of the axis 70. Preferably, the diameter of the second opening 82 is 10% to 15% bigger than the diameter of the axis 70. Thus, the second opening 82 is formed so that it allows the axis 70 to slightly deviate from its position. On the other hand, the first opening 81 is formed in such a way, that it allows part of the axis 70 to basically move in a direction vertical to the longitudinal axis 103 of the catheter shaft 2. More specifically, the first opening 81 is elongated in a direction vertical to the longitudinal axis 103 and preferably formed as a rounded rectangular, whose rounded corners each have a radius approximately equal to the radius of the axis 70. Due to this specific configuration of the first opening 81 and the second opening 82, pushing the axis 70 vertically in relation the longitudinal axis 103 of the catheter shaft 2 causes the axis 70 to slightly deviate from its position. The sizes of the first opening 81 and the second opening 82 are chosen in such a way, that the deviation of the axis 70 is so small that the transmission of a rotation of the rotating element 41 to the deflection element 3 is not impaired.

In FIG. 8 the axis 70 is shown in an intermediate position with regard to the first opening 81.

FIG. 9 shows a part of the stop mechanism 8 of FIG. 8.

In detail, a first gripping element 83 and a second gripping element 84 are provided inside the body 80. The first gripping element 83 and the second gripping element 84 are preferably positioned on diametrically opposed parts of an inner wall of the body 80. Further, the first gripping element 83 is directly arranged on the inner wall of the body 80, while the second gripping element 84 is connected to the inner wall of the body 80 via a spring element 85. The spring element 85 has in particular a first state and a second state. In its first state the spring element 85 is preferably partially compressed so that the spring element 85 pushes the axis 70 against the first gripping element 83 via the second gripping element 84. In its second state the spring element 85 is more, preferably fully, compressed than in its first state. In order for the spring element 85 to be brought from its first state into its second state, an external force applied by the user of the catheter assembly 1 is required.

Alternatively, the first state of the spring element 85 can correspond to the natural state of the spring element 85, where the spring element 85 is uncompressed. In this case the spring constant of the spring element 85 should most preferably be chosen so that the spring element 85 will not be compressed by the weight of the axis 70, should the catheter assembly 1 be oriented in such a way that the weight of the axis 70 acts on the spring element 85.

Both the first and the second gripping elements 83, 84 are advantageously formed by shape-complementary to the axis 70. Thus, the gripping elements 83, 84 can provide a tight grip on the axis 70. Especially, both the gripping elements 83, 84 are arranged at a side of the body 80 which faces the rotating button 7. This means that one of their ends is each closer to the side of the body 80 facing the rotating button 7. Preferably, the first gripping element 84 extends and is longer than the second gripping element 84 in the direction of the axis 70. More preferably, the first gripping element 83 extends over the whole length of the body 80 in the direction of the axis 70.

The first gripping element 83 is made of a material with a first friction coefficient at a surface of contact with the axis 70, while the second gripping element 84 is made of a material with a second friction coefficient at a surface of contact with the axis 70 which is lower than the first friction coefficient. This happens in order to allow to the axis 70 to rotate when in contact only with the second gripping element 84, whereas the axis 70 cannot rotate when in contact with the first gripping element 83. In other words, the first friction coefficient is chosen such that the axis 70 cannot rotate when in contact with the first gripping element 83, whereas the second friction coefficient is chosen such that the axis 70 is able to rotate when in contact with the second gripping element 84 but not in contact with the first gripping element 85.

The catheter shaft 2 may have a lining of lubricious material, such as Teflon, on its outer surface (outer lining) in order to reduce friction between the catheter shaft 2 and the body lumen and thus facilitate insertion of the catheter 1 into the body lumen. Such a lining of lubricious material can also be provided in the first lumen 23 on its inner wall (inner lining), so that movement of the guidewire 23 along the first lumen 23 is facilitated.

Furthermore, a first blocking element and/or a second blocking element are preferably provided. The first blocking element is configured to block the deflection element 3 from rotating in the first rotating direction beyond its end position. Hence, it can be ensured that no harm will be done to the guidewire 100 and due to that potentially also to the catheter 1, even if the user of the catheter assembly 10 accidentally tries to rotate the rotating button 7 to a position that would cause the deflection element 3 rotate further than its end position. Accordingly, the second blocking element is configured to block the deflection element 3 from rotating in the second rotating direction beyond its start position. By that it can be ensured that an over-rotation of the deflection element 3 in the second rotating direction 106 that could probably damage the guidewire 100 is not possible. The first and/or the second blocking elements are preferably arranged at the axis 70. Alternatively, the first and/or the second blocking elements are provided at the deflection element 3, more specifically at the main body 35.

In the following the use of the catheter assembly 10 will be explained with reference to FIGS. 1, 2, 3, 6, 8 and 9 in an endovascular application for a human patient.

In a first step the doctor chooses an entry point into the human's body for the catheter assembly 10. For example, the entry point can be the femoral artery.

After having made an incision, the doctor introduces the guidewire 100 into the lumen of the femoral artery and then the catheter assembly 10 is loaded on the guidewire 100 supporting and steering the guidewire 100 forward with the aim of reaching the affected target site. The catheter assembly 10, depending on the case, can be inserted inside the patient's body up to the handle 6 which always remains outside the patient's body and is thus accessible for manipulations by the doctor.

When the doctor comes across a branch on the way to the affected target site, the doctor operates the rotating button 7 in order to rotate the deflection element 3 and thus change the exit angle of the guidewire 100 through the shaft opening. Usually, the guidewire 100 is placed inside the catheter shaft 2 so that it extends through the first shaft opening 26 in the un-deflected state A. It is also possible that the guidewire 100 is placed in the catheter shaft 2 so that it does not extend through the first shaft opening 26 in the un-deflected state A. In this case, the guidewire 100 ends in the un-deflected state A before the first shaft opening 26.

In order to deflect the guidewire 100, the doctor pushes the rotating button 7 in the direction of the longitudinal axis 103 of the catheter shaft 2. By doing so, the second gripping element 84 is pushed by the axis 70 so that the spring element 85 is compressed. The axis 70 is then no longer in contact with the first gripping element 83. As long as this situation is maintained, the axis 70 can be rotated by rotating the rotating button 7. As the axis 70 connects the rotating button 7 with the rotating element 41, which is in turn operably connected via the controlling element 4 with the deflection element 3, the rotation of the rotating button 7 will cause a rotation of the deflection element 3. Due to its design the deflection element 3 will deflect the guidewire 100 thereby achieving the exit angle needed for entering into the body lumen branch.

More specifically, by rotating the deflection element 3 a force is applied through the distal edge 37 of the recess 30 to the guidewire 100 which together with the arrangement of part of the guidewire 100 in the first lumen 23 causes the guidewire 100 to deflect. When the guidewire 100 is deflected, the part of the guidewire 100 that is in the recess 30 is deformed so that it touches the bottom face 33 of the recess 30. Hence, during the rest of the deflection of the guidewire 100, sharp bends or kinks in the guidewire 100 are avoided.

Then, the doctor may remove its hand from the rotating button 7. As a result of this, the spring element 85 goes from its second state to its first state, where the axis 70 is pressed against the first gripping element 83 by the second gripping element 84. Thus, the position of the deflection element 3 and consequently the exit angle of the guidewire 100 are secured. Due to the specific choice of the first friction coefficient of the material of which the first gripping element 83 is made so that no rotation of the deflection element 3 occurs, when the axis 70 is pressed against the first gripping element 83 by the second gripping element 84, the exit angle of the guidewire 100 can be secured without the need of the doctor holding the rotating button 7.

Then, the doctor can push the guidewire 100 further into the branch in order to reach the affected target site.

If during the adjustment of the exit angle of the guidewire 100 the doctor rotates the deflection element 3 more than needed (but still in the allowable range), has accidentally rotated the deflection element 3 when not required or if for some reason the procedure has to be abandoned, the doctor can rotate the rotating button 7 in the second rotating direction 106 to bring the deflection element 3 either to the wished position or its initial position, respectively.

The return of the guidewire 100 may happen due to its elastic properties and/or to the guiding element 31, which applies a force to the guidewire 100.

In the case that the catheter assembly 10 is placed in the lumen in a different orientation that what is needed for entering the branch, the doctor may turn the catheter assembly 1 around the longitudinal axis 103 of the catheter shaft 2 before entering the branch till the needed orientation is achieved. Then, the doctor may operate the rotating button 7, as described above.

It is noted that the stop mechanism 8 is optional and can thus be omitted. In this case, the doctor may have to stabilize the rotating button 7 by his/her hand, as the guidewire 100 usually has elastic properties and tends to return to its un-deflected state if no force is applied thereto anymore.

The catheter assembly 10 with the catheter 1 according to the present invention facilitates the exact positioning and crossing of a guidewire through significant tortuous body lumens, branch orifices with high angulation and generally helps in all cases where the guidewire needs the maximal possible steering support of the catheter. The catheter can have several applications in the treatment of pathologies by catheterisation of arteries and veins as well as other lumens of the human body, including the ureter and urethra, the cholangi, the esophagus and the tracheobronchial tree. It may also be used for the deployment of embolisation materials, such as coils, or even as an aid for the re-entry of the wire into the true lumen of the vessel during a sub-intimal technique procedure. It can also be understood that the catheter of the present invention can be used not only for humans but also animals, where a catheterization is applied as a technique.

FIG. 13 shows a deflection element 3 of a catheter assembly 10 according to a second embodiment of the present invention.

The main difference of the catheter assembly 10 according to the second embodiment from the one of the first embodiment lies in the shape of the main body 35 of the deflection element 3. In this case the main body 35 is substantially formed as a cylinder. In more concrete terms, the outer shape of the main body 35 is substantially a cylinder. More specifically, the main body 35 is barrel-shaped. A barrel is a cylinder bulging in a middle portion between the cylinder bases. The cylinder axis preferably extends in the direction of the rotational axis 102 of the deflection element 3.

The cylindrical or barrel shape of the deflection element 3 can be advantageous over the spherical design of the deflection element 3 according to the first embodiment due to its more compact size. Thus, for the same size of the guidewire 100 and consequently for the same size of the recess 30, a smaller deflection element 3 is needed. This enables the reduction of the overall size of the catheter 1, more specifically of the tip 21 of the catheter shaft 2 but thus in general the catheter shaft 2. Therefore, the catheter 1 according to the second embodiment can be used in even smaller lumens in the human body.

FIGS. 14 and 15 show a tip 21 of a catheter assembly 10 according to a third embodiment of the present invention.

In the tip 21 of the catheter assembly 10 according to the third embodiment the shaft opening comprises only the first shaft opening 26 at the distal end 27 of the catheter shaft 2. The tip 21 is arranged in such a way that the dimension of the tip 21 in the direction of the longitudinal axis 103 of the catheter shaft 2 is approximately the same as the dimension of the deflection element 3 in the direction of the longitudinal axis 103. The deflection element 3 is configured to deflect the guidewire 100 through the first shaft opening 26.

In addition to the foregoing description of the present invention, for an additional disclosure explicit reference is taken to graphic representation of FIGS. 1 to 15.

An idea for an endovascular remotely steerable guidewire catheter is described as follows:

The idea refers to minimally invasive surgical devices and methods, and specifically to endovascular catheters, the purpose of which is the steering of the guidewire, as well as useful vascular intervention methods during endovascular surgery. Specifically, the present idea relates to endovascular steerable guidewire catheters that are used for the precise positioning of the guidewire within the target vessel or the crossing of the guidewire through significant tortuosity, demanding vascular bifurcation, and generally in cases where the guidewire needs the catheter to provide the best possible steering.

Endovascular surgery is a useful and effective method of dealing with most types of vascular diseases. Generally, the appropriate endovascular device is inserted into the patient's circulatory system, and guided through the vessels, reaches the target lesion. With the use of endovascular surgery we can reach most parts of the patient's circulatory system, including the heart's coronary vessels, the brain vessels and the peripheral vessels.

Endovascular surgery is a minimally invasive surgical method that was designed to reach, diagnose and treat vessels from within. The recanalization of stenoses or blocked vessels is achieved without the use of general anesthesia, long hospitalization and considerable postoperative pain.

Angioplasty, with or without the deployment of a stent is used for the treatment of chronic blockages, stenoses and other vessel pathologies. During the angioplasty of the coronary, brain or peripheral vessels, an endovascular catheter placed over a guidewire is led to the desired area via the patient's circulatory system. Next, the guidewire, supported by the catheter, is guided through the distal opening of the catheter into the target artery (e.g. coronary, brain, renal artery etc.) until it crosses the stenosis or blockage in need of treatment. Following that, a balloon catheter is moved forward over the guidewire that has already crossed the stenosis and is carefully positioned within the blockage. After the catheter has been carefully positioned, the balloon is inflated to a predefined width, pushing the atheromatic material that causes the blockage outwards and opening the artery. The balloon is then deflated, the blood begins to circulate via the opened artery, and the balloon catheter is removed. When needed, after the artery has been opened, a stent may be deployed at the point of the stenosis in order to keep the vessel open for a longer period of time.

Endovascular catheters with or without the ability to remotely steer the guidewire have been used for years in most endovascular applications and are a basic tool in these treatment approaches. Today, many such different catheters are known and used, and each has certain advantages but also disadvantages. For this reason, there is a great need to develop alternative innovative guide catheters that will have the advantages of the older ones but will be improved regarding their disadvantages, acquiring greater and new potential.

Endovascular guide catheters are necessary tools in endovascular surgery, one of their most important uses is the backup support and the steering of the guidewire in the surgeon's effort to cross through the stenosis—vessel blockage with it. This step proves quite difficult in the cases with important tortuosity, bifurcation and vasculature disorders and generally in cases where the guidewire needs the catheter to provide the maximum possible steering support.

Today, there are endovascular guide catheters that use modern materials and development techniques that achieve improved characteristics.

A guide catheter's most important characteristics are:
1. Pushability: the degree in which the force transmitted from the proximal end of the catheter is translated into the movement of its tip, which depends on the transmission of the force along the body of the catheter.
2. Trackability: the ability of a catheter to follow the guidewire in tortuous vasculature, which depends on the diameter, length and elasticity of the catheter, as well as the resistance caused by friction.
3. Steering (rotation) ability: the ability to steer the guide catheter's tip (High Torque Control), which essentially means a high resistance to bending—folding during its rotation within the vessel.
4. Atraumatic distal tip that protects the vessel's endothelium from damage.

Today, many different guide catheters are used in endovascular surgery, each with the above mentioned characteristics to a greater or lesser degree. An important limitation to the use of these catheters is low profile blood vessels that do not allow the guide catheters to be maneuvered within the vessel so as to steer the guidewire. Additionally, most guide catheters have a pre-shaped distal tip in order to facilitate particular catheterization angles. That means that the surgeon must choose beforehand the catheter—or the combination of catheters—that will be used during the procedure.

The idea aims to the creation of an endovascular remotely steerable guidewire catheter, as described above, that will collectively and maximally presents the advantages of an ideal catheter.

A catheter easy to build and use that will provide the guidewire with maximal steering potential—when needed—but will not lack pushability and trackability over a guidewire in tortuous vasculature.

According to the idea this is achieved with the development of an endovascular guide catheter, which, at its distal end, incorporates a custom-designed spherical mechanism that has the ability to rotate around an axis. The rotation of the spherical mechanism is accomplished with the help of a rotating button on the ergonomically designed handle of the guide catheter and an inner circuit of synthetic threads that runs along most of its length.

A guide catheter that incorporates at its distal end a custom-designed spherical mechanism that can rotate around an axis changes the picture, providing the new guide catheter with great remote steering abilities of the guidewire.

The custom-shaped rotating spherical mechanism that is incorporated in the distal end of the guide catheter changes the exit angle of the guidewire. In this way the guidewire can exit the distal end of the catheter forming at will a wide range of angles in relation to the central axis of the guide catheter. This practically means that the guidewire can be accurately steered through big angulations, with a high performance even within very low profile vessels, because the distal end does not have to be angled to steer the guidewire. A procedure can be performed with the use of one and only guide catheter, since it can replace all the rest that have a pre-shaped exit angle for the guidewire.

With this innovation, the new guide catheter can support and steer the guidewire in the effort to move through anatomically hard to cross regions of the vessels or other lumens of the human body, while—at the same time—accurately readjusting the exit angle of the guidewire.

By using the same methodology, the present invention can be modified by loading other endovascular tools such as embolization coils and facilitate their placement within the vessel, or even contribute with its steering in the reentry of the guidewire into the true lumen during a subintimal technique procedure.

In the figures that follow, the corresponding reference numbers refer to the same parts, from all different angles. The figures are not drawn necessarily in scale. Instead, the presentation of the principles of the idea has been emphasized. The figures represent typical applications of the idea and should not therefore be considered limiting as to the range of applications. The idea will be described and explained with additional details and accuracy with the use of the attached figures, where:

FIG. 1 and FIG. 2 are detailed illustrations of the endovascular guide catheter and of the inner synthetic thread circuit, that depict the controlled rotation of the custom-designed spherical mechanism that is incorporated in the distal end of the catheter, as well as its remote steering handle. The result is the change in the exit angle of the guidewire, according to the general principles of the idea.

FIGS. 3 and 4 are a complete illustration of the non-mobile and the mobile components of the endovascular remotely steering guidewire catheter with the simultaneous representation of their inner lumens. It should be noted that for the tracking of the device during the endovascular process, some of the illustrated catheter's parts are made of radiopaque material among other materials. More specifically, FIG. 3 is an illustration of the arrangement of the parts of the guide catheter and its custom-designed handle, along with an illustration of their inner lumens. More specifically, FIG. 4 an illustration of the custom-designed handle of the guide catheter with the rotating remotely steering button and of the cylindrical longitudinal catheter in detail, both inside and outside.

FIG. 5 illustrates the mobile parts of the endovascular guide catheter at an angle. Specifically, it depicts the custom-designed spherical mechanism that is incorporated at the distal end of the catheter along with the rotating remotely steering ring, as well as part of the inner circuit of synthetic thread that facilitates the rotation of the custom-designed spherical mechanism and part of the guidewire.

It is understood that the figures are diagrammatic and schematic representation of exemplary applications of the device and are not limiting as to the range of applications. They are also not drawn in scale.

As further described below, the present device generally refers to endovascular catheters and methods of using them. More specifically, the present device relates to endovascular guide catheters that facilitate the exact positioning and crossing of a guidewire through significant tortuous vasculature, bifurcation lesions and generally help in all cases where the guidewire needs the maximal possible steering support of the catheter. It should be noted that this description is only used as an example and that the present endovascular guide catheter can have several applications in the treatment of pathologies in various lumens of the human body, including the ureter and urethra, the cholangi, the esophagus and the tracheobronchial tree.

The endovascular remotely steering guidewire catheter, as illustrated in FIG. 1 and in FIG. 2, has been designed for endoluminal crossing through a vessel and for this reason it can acquire the size that will facilitate this crossing, depending on the vessel in question. For example, the use in non coronary vessels demands catheter dimensions of a greater scale than the one used for a coronary artery.

Figure 3:
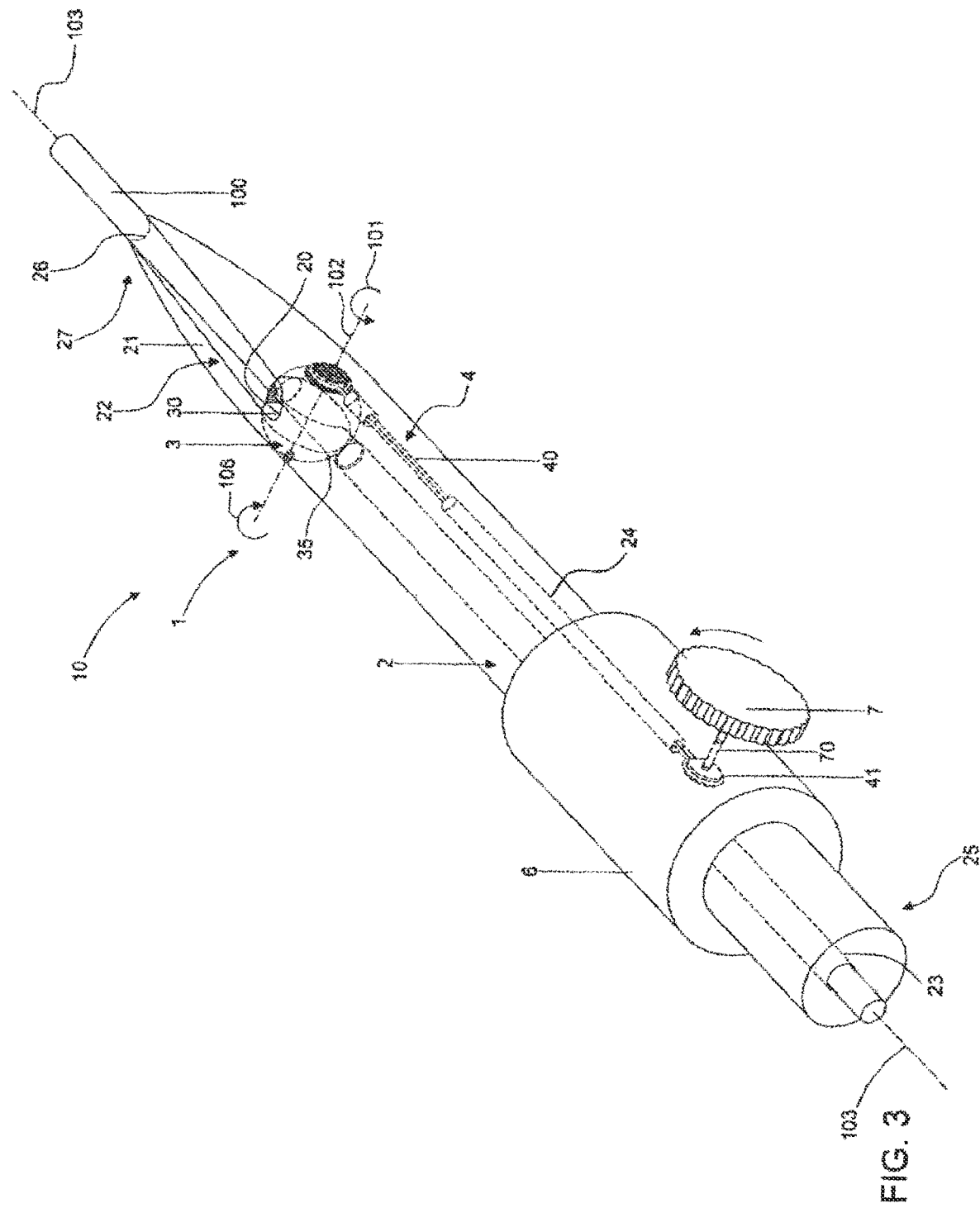
Figure 4:
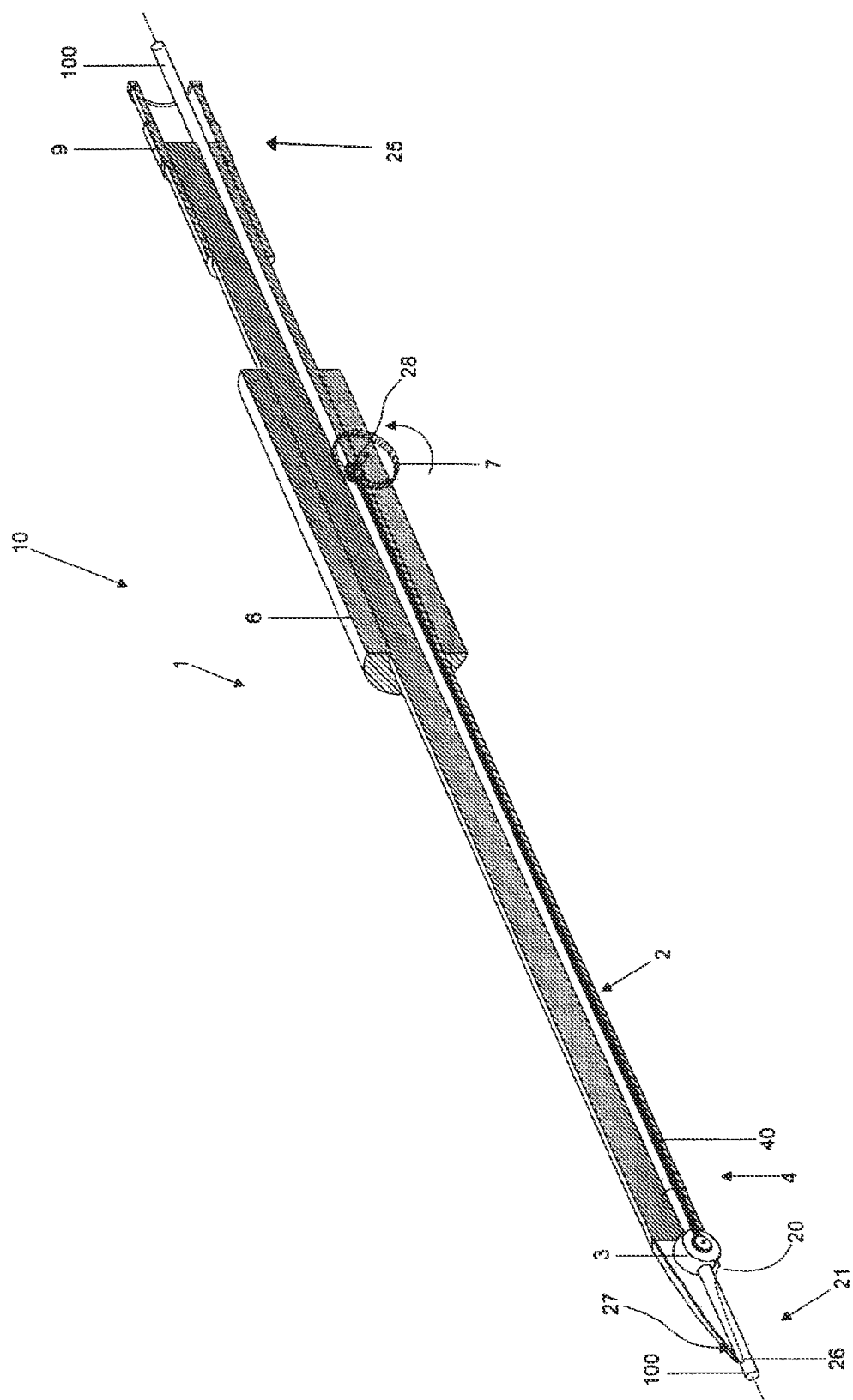
Figure 10:
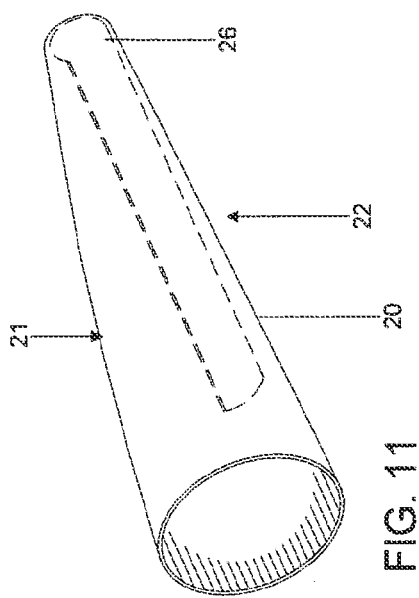
FIGS. 10 and 11 are an illustration of the custom-shaped tip with its groove at the distal end of the guide catheter from a different angle.
Figure 11:
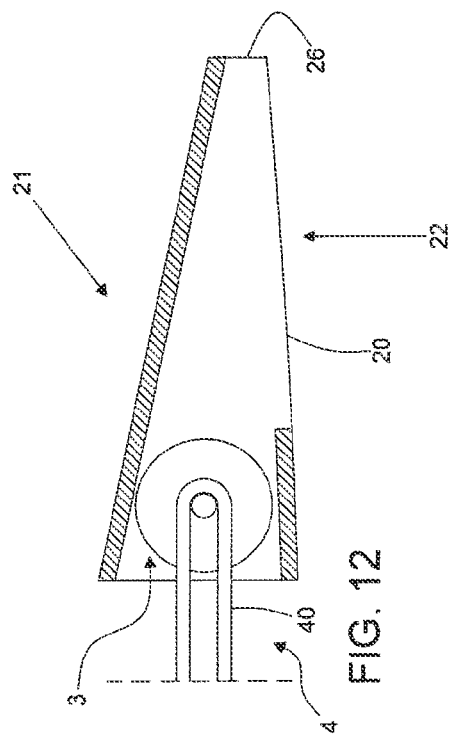
Figure 12:
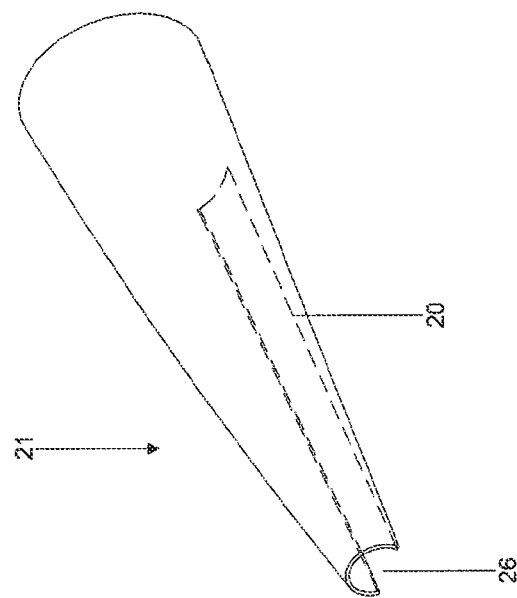

As illustrated in FIG. 1, FIG. 2 and FIG. 3, the endovascular remotely steering guidewire catheter consists of a longitudinal cylindrical catheter (FIG. 3), also made of radiopaque material, at the central part of which the handle is attached, along with the rotating remotely steering button (FIG. 3 and FIG. 4) of the custom designed spherical mechanism that is incorporated in the custom-shaped tip, at its distal end (FIGS. 3, 10 and 11). The inner thread circuit includes the custom-designed thread that connects the rotation disc of the rotating remotely steering button (FIG. 1, FIG. 2) with the rotation disc of the custom-designed spherical mechanism that is incorporated in the custom-shaped tip at the distal end of the guide catheter (FIG. 3).

As further described below, the idea consists of mobile and non mobile components.

Non Mobile Components

As illustrated in FIG. 3, the cylindrical longitudinal catheter consists of three connecting parts and includes a main cylindrical part that comprises the central opening and part of the lumen, through which the guidewire passes, a cylindrical part that includes the whole of the inner lumen, its main opening out of which the synthetic thread exits the lumen, and the cylindrical longitudinal catheter and part of the inner lumen. The distal part includes a custom-shaped tip in which the custom designed spherical mechanism is incorporated (FIG. 1, FIG. 2, FIG. 5, FIG. 6, FIG. 3, FIG. 10, FIG. 11) at the end of the cylindrical longitudinal catheter. During the endovascular use, the Endovascular Remotely Steerable Guidewire Catheter (FIG. 3, FIG. 4), can be inserted into the human body through its custom-designed tip, up to the handle, which remains at all times outside the human body and is accessible to the surgeon.

The cylindrical longitudinal catheter (FIG. (3)) includes the main opening of the inner lumen that runs along its full length, beginning at the opening of the catheter and ending at the last opening of channel of its custom designed tip. Within the inner lumen, runs the guidewire during the use of the cylindrical longitudinal catheter, while through the inner lumen runs the synthetic thread in the form of a closed circuit (FIG. 1, FIG. 2) that transfers the movement from the rotating button to the custom-designed spherical mechanism (FIG. 3).

The custom-designed tip includes channel and has a conical shape so as to move along the vessel with ease. It also includes the groove that is essentially the exposure of channel, through which the guidewire can exit at an angle in relation to the main catheter axis (FIGS. 10, 11).

The cylindrical longitudinal catheter includes from one to two inner lumens at its various parts. These inner lumens are parallel to one another and cover the inner part of the catheter as illustrated in the drawings of the apparatus (FIG. 3).

Mobile Parts

Figure 7:
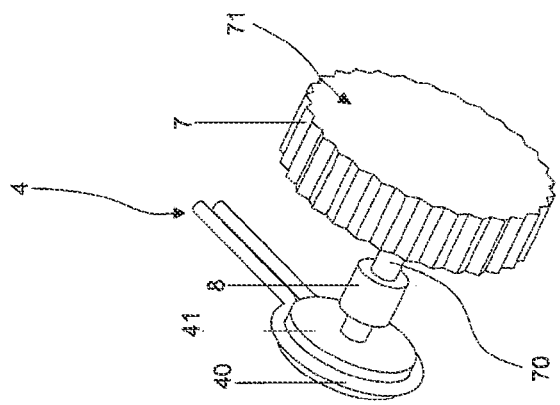
FIG. 7 is an illustration of the rotating remotely steering button, of the custom-designed spherical mechanism, of its rotation ring, as well as part of the synthetic threads attached to—wound around the rotation disc.
Figure 6:
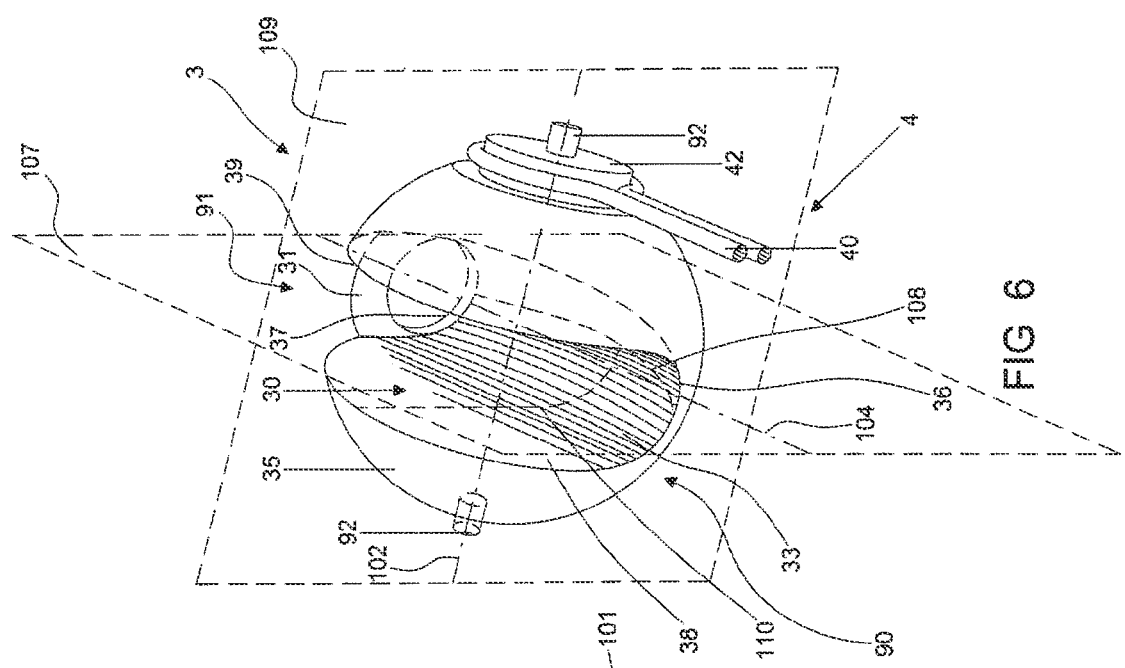
FIG. 6 illustrates the custom-designed spherical mechanism that is incorporated at the distal end of the catheter along with the rotating remotely steering ring, as well as part of the inner circuit of synthetic thread that facilitates the rotation of the custom-designed spherical mechanism without the guidewire.
Figure 5:
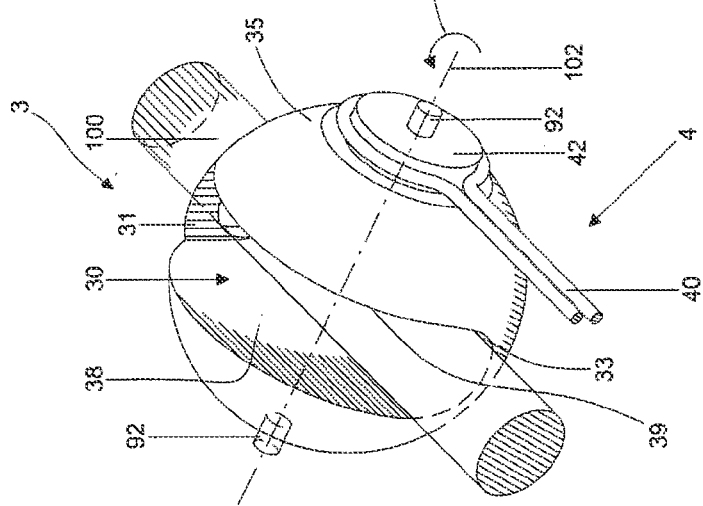
Figure 13:
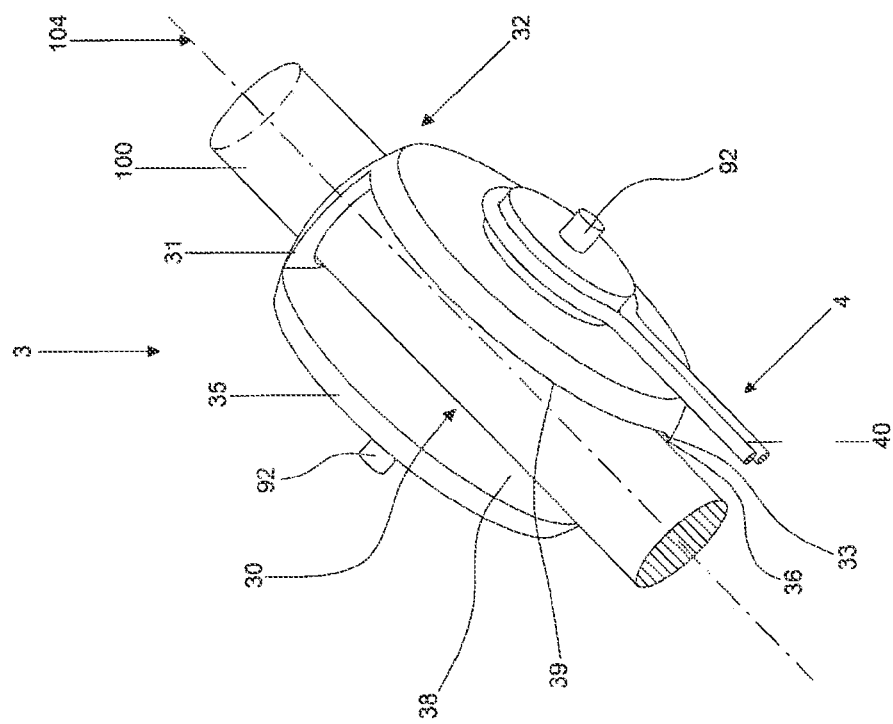
FIG. 13 is an illustration of a variation of the custom-designed spherical mechanism in cylindrical form that can be incorporated at the distal end of the catheter along with the rotating remotely steering ring, as well as part of the inner circuit of the synthetic thread that facilitates its rotation, with the illustration of the guidewire.
Figure 14:
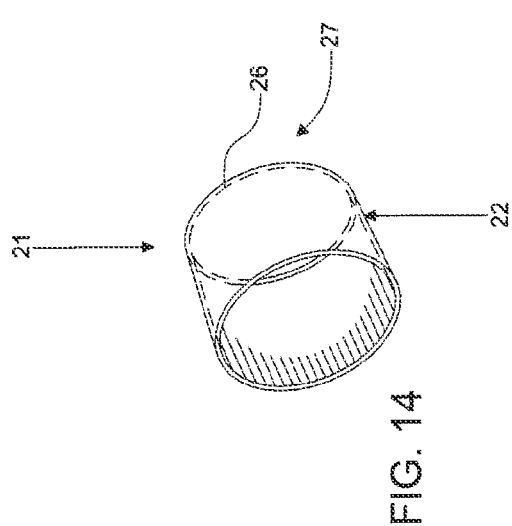
Figure 15:
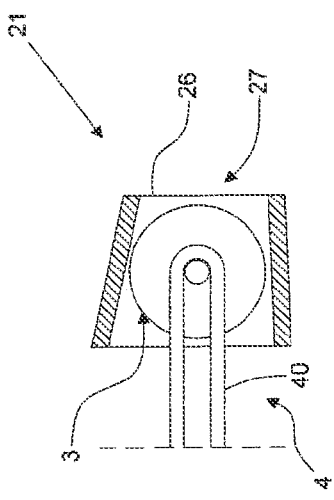

As illustrated in FIG. 1, FIG. 2, FIG. 4, FIG. 5, FIG. 6, FIG. 7, FIG. 3, FIG. 10 and FIG. 11, the endovascular remotely steerable guidewire catheter also includes mobile parts. The mobile parts are attached to the cylindrical part and the distal part of the cylindrical longitudinal catheter (FIG. 3). The cylindrical part includes the rotating button (11) that is attached to the handle and which facilitates the remote steering of the wire of the guide catheter (FIG. 1, FIG. 2, FIG. 7, FIG. 3, and FIG. 4). The distal part includes the custom-designed spherical mechanism (14) (FIG. 5, FIG. 6) that is incorporated in the custom-shaped tip and can rotate around its axis at the distal end of the guide catheter (FIG. 1, FIG. 2 and FIG. 3, and FIG. 4), offering the option of choosing the exit angle of the guidewire from the guide catheter after it exits the distal end of the inner lumen via the groove, the exit ring of the spherical mechanism and the channel of the custom-designed tip. The exit ring is formed by the distal part of the groove and the exit bridge (FIG. 5, FIG. 6). At the custom-designed spherical mechanism that is incorporated at the tip of the guide catheter (25) we find attached its rotating disc and the braces as illustrated in FIG. 5 and FIG. 6. Around the rotating disc the thread is wound, in the form of a closed circuit (FIG. 1, FIG. 2, FIG. 5, FIG. 6, and FIG. 3), that connects it to the rotation disc of the rotating button in a relative movement (FIG. 1, FIG. 2, and FIG. 7). The range of the angle that the custom-designed spherical mechanism (FIG. 1, FIG. 2) rotates is around 170 degrees. Instead of the custom-designed spherical mechanism, a variation of it can be used, the custom-designed cylindrical mechanism (FIG. 13).

The shape of the custom-designed tip at the distal end of the remotely steerable guidewire catheter is conical with a groove along its length (FIGS. 10, 11 FIG. 3) that allows the exit of the guidewire at an angle in relation to the main axis of the guide catheter.

This new endovascular remotely steerable guidewire catheter can have one external and one internal lining of lubricious material, such as Teflon.

The idea of the endovascular remotely steerable guidewire catheter can be DEFINED by the following clauses:

CLAUSES

1. The Endovascular Remotely Steerable Guidewire Catheter consists of:
   a cylindrical longitudinal catheter, developed also by radiopaque material, that is comprised of three interconnecting parts and includes a proximal cylindrical part that consists of the proximal opening of the inner lumen, where the guidewire passes through, a cylindrical part that incorporates part of the inner lumen and the whole of the inner lumen. The proximal opening of the inner lumen communicates with the outer surface of the cylindrical longitudinal catheter via the opening that is found on the body of the cylindrical longitudinal catheter close to the main opening of the inner lumen. Last, a custom-designed tip is found at the distal part of the cylindrical longitudinal catheter. The cylindrical longitudinal catheter includes two inner lumens, which are parallel to one another and to the main axis of the cylindrical longitudinal catheter. The custom-designed handle with the rotating remotely steering button envelops parts of the cylindrical parts. At the distal part of the cylindrical longitudinal catheter, and in particular within its custom-designed tip, the custom-designed spherical mechanism for the steering of the guidewire is incorporated. Alternatively, the custom-designed spherical mechanism can have the form of a cylindrical mechanism. The movement of the rotating button and the custom-made spherical mechanism is dependent, since with the rotation of the button around its main axis, the spherical mechanism rotates around its axis. The rotation angles of the button and the spherical mechanism are not typically the same, but they are in a standard and dependent correlation/linked relationship. During a surgical procedure, the cylindrical longitudinal catheter is inserted into the patient via its custom-made tip, up to the custom-designed handle, which is outside the human body, accessible for surgical manipulations by the doctor.

2. The endovascular remotely steerable guidewire catheter according to clause 1 is characterized by the fact that the rotating button and the custom-designed spherical mechanism are connected to each other with synthetic thread in the form of closed inner circuit. Indeed, the rotating button and the custom-designed spherical mechanism are connected to each other with the inner circuit of the synthetic thread through their rotating discs. The synthetic rotation thread, in the form of closed circuit, passes through the inner lumen and ends up at the rotation discs, which are placed close to the two openings/mouths of the inner lumen, where they are wound.

3. According to clause 2, the endovascular remotely steerable guidewire catheter is characterized by the fact that the synthetic rotation thread is wound up in the form of closed circuit around the rotation discs of the rotating button and the custom-designed spherical mechanism, in such a way as to transfer the rotating movement of the first to the latter in the same direction in some kind of standard correlation. That is, by rotating the rotating button at an angle φ, the custom-made spherical mechanism also rotates at the same time at an angle X by φ, where X is some intended number.

4. The custom-designed spherical mechanism according to clause, 1 consists of a sphere, at the center of which a through lumen has been opened. This lumen can be curved, while it extends widthwise towards its curved part until it is completely exposed, creating a groove. At the distal end of the groove of the spherical mechanism (14) the exit ring can optionally be placed, created by the bridge, through which the guidewire passes.

5. According to clause 1, the custom-designed cylindrical mechanism, which can be used instead of the spherical mechanism (14), consists of a cylinder at the center of which a through lumen has been opened. This lumen can be curved, while it extends widthwise towards is curved part until it becomes completely uncovered/conspicuous, creating a groove (v shape), u shape cut. At the distal end of the cut of the cylindrical mechanism the exit ring can optionally be placed, created by the bridge, through which the guidewire passes.

6. According to clause 1, the custom-designed tip incorporates at its wide part the custom-designed spherical mechanism which is affixed with the help of braces in a way so that the inner lumen is always in alignment and communication with the groove, during the whole breadth of the rotation around its axis. In this way, the guidewire coming out of the distal opening of the inner lumen is always inserted in the groove and forwarded within the exit ring. Additionally, the synthetic thread exiting the peripheral opening of the inner lumen in the form of a closed circuit is wound around the rotation ring. In this way, the change in the exit angle of the guidewire is achieved with the rotation of the custom-designed spherical mechanism, through the rotation ring, at the desired angle. Additionally, the custom-designed tip carries the groove that creates the channel that is basically the continuation of the inner lumen at the distal part that has been exposed, so that the guidewire can come out of the guide catheter at an angle.

7. According to clause 1, the custom-designed handle of the guide catheter envelops the cylindrical longitudinal catheter in the cylindrical parts. It incorporates the rotating remote steering button, the axis and the rotation disc, which is found near the opening where the synthetic thread comes out in the form of a closed circuit and is wound up in the rotation disc.

8. According to clause 1, the endovascular remotely steerable guidewire catheter can be used for the catheterization of arteries and veins, as well as other lumens in the bodies of animals or people, such as the cholangi, urinary lumens, lumens of the tracheobronchial tree etc. It can also be used for the deployment of embolization materials or can even be used as an aid for the reentry of the wire within the true lumen during a subintimal technique procedure.

LIST OF REFERENCE SIGNS 1 catheter/(endovascular remotely steering catheter)
2 catheter shaft/(cylindrical longitudinal catheter)
3 deflection element/(custom-designed spherical/cylindrical mechanism)
4 controlling element/(custom-designed thread, synthetic thread)
5 adapter
6 handle/(custom-designed handle)
7 rotating button or knob/(rotating remotely steering button)
8 stop mechanism
10 catheter assembly
20 second shaft opening/(channel)
21 tip/(custom-shaped tip)
22 peripheral area of the catheter shaft
23 first lumen/(inner lumen)
24 second lumen/(inner lumen)
25 proximal end of the catheter shaft
26 first shaft opening
27 distal end of the catheter shaft
28 third lumen
30 recess/(groove)
31 guiding element/(bridge, exit bridge)
33 bottom face of the recess
34 rotating disc of deflection element
35 main body of deflection element
36 proximal edge of the recess (bottom face)
37 distal edge of the recess (bottom face)
38 first wall of the recess
39 second wall of the recess
40 closed-loop transmission element
41 rotating element (first rotating disc)/(rotation disc)
42 second rotating disc
70 axis
71 orientation indicator
80 body of stop mechanism
81 first opening
82 second opening
83 first gripping element 84 second gripping element
85 spring element
90 proximal end of the deflection element
91 distal end of the recess
92 support/(brace)
100 guidewire/(guidewire, wire)
101 first rotating direction
102 rotational axis
103 longitudinal axis of the catheter shaft
104 longitudinal axis of the recess
105 angle of rotation of the deflection element
106 second rotating direction
107 first plane of curvature
108 first intersection
109 second plane of curvature
110 second intersection
111 arrow
112 arrow

The invention claimed is:

1. An endovascular catheter configured for tortuous vasculature, the endovascular catheter comprising:
 a catheter shaft including a first lumen and a shaft opening, wherein the first lumen is in communication with the shaft opening,
 a semi-spherical deflector rotatably arranged inside the catheter shaft and configured to rotate to deflect a guidewire through the shaft opening, and
 a closed-loop transmission element that is operably connected with the semi-spherical deflector and configured to rotate the semi-spherical deflector in a first rotating direction, wherein the semi-spherical deflector comprises a recess formed in a direction of a longitudinal axis of the catheter shaft, and wherein a guiding element configured to guide the guidewire is arranged at a distal end of the recess, wherein the guiding element is formed as a ring, arranged in such a way that a central axis of the ring coincides with a longitudinal axis of the recess.

2. The endovascular catheter according to claim 1, wherein the semi-spherical deflector is configured to rotate around a rotational axis which is vertical to the longitudinal axis of the catheter shaft.

3. The endovascular catheter according to claim 1, wherein the closed-loop transmission element is configured to transmit a rotation from a rotating element to the semi-spherical deflector, wherein the rotating element is operably connected to the closed-loop transmission element.

* * * * *